United States Patent [19]
Van Der Ley et al.

[11] Patent Number: 5,705,161
[45] Date of Patent: Jan. 6, 1998

[54] IMMUNOGENIC MENINGOCOCCAL LPS AND OTHER MEMBRANE VESICLES AND VACCINE THEREFROM

[75] Inventors: Peter André Van Der Ley, Utrecht; Jan Theunis Poolman, Broek in Waterland; Peter Hoogerhout, Bilthoven, all of Netherlands

[73] Assignee: De Staat der Nederlanden, Vertegenwoordigd Door de Minister Van Welzijn, Volksgezondheid en Cultuur, Rijswijk, Netherlands

[21] Appl. No.: 411,727

[22] PCT Filed: Jul. 30, 1993

[86] PCT No.: PCT/NL93/00163

§ 371 Date: May 1, 1995

§ 102(e) Date: May 1, 1995

[87] PCT Pub. No.: WO94/08021

PCT Pub. Date: Apr. 14, 1994

[30] Foreign Application Priority Data

Oct. 2, 1992 [NL] Netherlands ............... 9201 716

[51] Int. Cl.$^6$ .................. A61K 39/095; A61K 45/00; C07H 1/00; C12N 15/00
[52] U.S. Cl. ................... 424/250.1; 424/282.1; 536/123.1; 435/72; 435/172.1
[58] Field of Search ............ 536/123.1; 424/282.1, 424/250.1; 435/69.1, 72, 172.1, 91.32

[56] References Cited

FOREIGN PATENT DOCUMENTS

WO 90/06696  6/1990  WIPO.

OTHER PUBLICATIONS

E. Wiertz et al., "T Cell Recognition of *Neisseria meningitidis* Class 1 Outer Membrane Proteins", The Journal of Immunology, Sep. 15, 1991, vol. 147, No. 6, pp. 2012–2018.

A. Verheul et al., "Minimal Oligosaccharide Structures Required for Induction of Immune Responses against Meningococcal Immunotype L1, L2, and L3, 7, 9 Lipopolysaccharides Determined by Using Synthetic Oligosaccharide–Protein Conjugates", Infection and Immunity, Oct. 1991, vol. 59, No. 10, pp. 3566–3573.

A. Verheul et al., "Preparation, Characterization, and Immunogenicity of meningococcal Immunotype L2 and L3, 7, 9 Phosphoethanolamine Group–Containing Oligosaccharide–Protein Conjugates", Infection and Immunity, Mar. 1991, vol. 59, No. 3, pp. 843–851.

M. Frosch et al., "Molecular characterization and expression in *Escherichia coli* of the gene complex encoding the polysaccharide capsule of *Neissaria meningitidis* group B", Microbiology, Mar. 1989, vol. 86, pp. 1669–1673.

G. Boons et al., "Preparation of a Well–Defined Sugar–Peptide Conjugate: A Possible Approach to a Synthetic Vaccine Against *Neisseria meningitidis*", pp. 303–308.

C. Frasch, "Vaccines for Prevention of Meningococcal Disease", Clinical Microbiology Reviews, Apr. 1989, vol. 2, pp. S134–S138.

Verheul et al, Micro. Rev., Mar. 1993, 57(1):34–49.

Robertson et al., Molec. Microbio, 1993, 8(5):891–901.

*Primary Examiner*—James C. Housel
*Assistant Examiner*—Jennifer Shaver
*Attorney, Agent, or Firm*—Young & Thompson

[57] ABSTRACT

The invention is directed to an immunity providing B cell activating molecule derived from a meningococcal lipopolysaccharide (LPS) having at least one epitope, said molecule comprising at least the communal part of the oligosaccharide part (core region) of lipopolysaccharides specific for at least two meningococcal immunotypes, preferably immunotypes L2 and L3 and wherein in galactose is absent in the B cell activating part, as well as derivatives of the molecules with immuno reaction inducing capacity. The invention is also directed at an outer membrane vesicle provided with a group of polypeptides having at least the immunoactivity of outer membrane proteins (OMP's) bound to a membrane, a polypeptide from the group of said outer membrane vesicles being a membrane anchored OMP or OMP fragment with a mutation in one of the surface loops, preferably in a 2, 3, 5, 6, 7 or 8-loop of a class I OMP. Furthermore, the invention is directed at a vaccine comprising such an outer membrane vesicle and/or lipopolysaccharide, as well as methods for preparing a lipopolysaccharide and an outer membrane vesicle as described above.

13 Claims, No Drawings

SEQUENCE LISTING ( 1 ) GENERAL INFORMATION:

( i i i ) NUMBER OF SEQUENCES: 30

( 2 ) INFORMATION FOR SEQ ID NO:1:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 2..34

( x i ) SEQUENCE DESCRIPTION: SEQ ID NO:1:

```
G AAC GGC GGC GCC TCT GGC CAA GTT AAA GTT ACT AGTAC          39
  Asn Gly Gly Ala Ser Gly Gln Val Lys Val Thr
  1           5                   10
```

( 2 ) INFORMATION FOR SEQ ID NO:2:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Asn Gly Gly Ala Ser Gly Gln Val Lys Val Thr
1               5                   10
```

( 2 ) INFORMATION FOR SEQ ID NO:3:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 2..34

( x i ) SEQUENCE DESCRIPTION: SEQ ID NO:3:

```
T AGT AAC TTT AAC TTG GCC AGA GGC GCC GCC GTT CGTAC          39
  Ser Asn Phe Asn Leu Ala Arg Gly Ala Ala Val
  1           5                   10
```

( 2 ) INFORMATION FOR SEQ ID NO:4:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Ser Asn Phe Asn Leu Ala Arg Gly Ala Ala Val
1               5                   10
```

( 2 ) INFORMATION FOR SEQ ID NO:5:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

```
GGTACGAACG GC                                                12
```

( 2 ) INFORMATION FOR SEQ ID NO:6:

( i ) SEQUENCE CHARACTERISTICS:
        ( A ) LENGTH: 12 base pairs
        ( B ) TYPE: nucleic acid
        ( C ) STRANDEDNESS: single (D) TOPOLOGY: linear (ii) MOLECULE TYPE: DNA (genomic)

(xi) SEQUENCE DESCRIPTION: SEQ ID NO:6:

GCCGTTCGTA CC                                                                                          12

(2) INFORMATION FOR SEQ ID NO:7:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

GTTACTAGTA CC                                                                                          12

(2) INFORMATION FOR SEQ ID NO:8:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

GGTACTAGTA AC                                                                                          12

(2) INFORMATION FOR SEQ ID NO:9:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 2..34

(xi) SEQUENCE DESCRIPTION: SEQ ID NO:9:

G TAT ACC AAA GAC ACC AAC AAC AAC TTG ACC TTG AGTAC                                                    39
  Tyr Thr Lys Asp Thr Asn Asn Asn Leu Thr Leu
   1               5                      10

(2) INFORMATION FOR SEQ ID NO:10:

(i) SEQUENCE CHARACTERISTICS:
        (A) LENGTH: 11 amino acids
        (B) TYPE: amino acid
        (D) TOPOLOGY: linear (ii) MOLECULE TYPE: protein (xi) SEQUENCE DESCRIPTION: SEQ ID NO:10:

Tyr Thr Lys Asp Thr Asn Asn Asn Leu Thr Leu
 1             5                   10

(2) INFORMATION FOR SEQ ID NO:11:

(i) SEQUENCE CHARACTERISTICS:
        (A) LENGTH: 39 base pairs
        (B) TYPE: nucleic acid ( C ) STRANDEDNESS: single
                    ( D ) TOPOLOGY: linear ( i i ) MOLECULE TYPE: DNA (genomic)

( i x ) FEATURE:
                    ( A ) NAME/KEY: CDS
                    ( B ) LOCATION: 2..34

( x i ) SEQUENCE DESCRIPTION: SEQ ID NO:11:

T  CAA  GTT  CAA  GTT  GTT  GTT  GTT  GTC  TTT  GGT  ATA  CGTAC            3 9
   Gln  Val  Gln  Val  Val  Val  Val  Val  Phe  Gly  Ile
    1              5                        10

( 2 ) INFORMATION FOR SEQ ID NO:12:

( i ) SEQUENCE CHARACTERISTICS:
                    ( A ) LENGTH: 11 amino acids
                    ( B ) TYPE: amino acid
                    ( D ) TOPOLOGY: linear ( i i ) MOLECULE TYPE: protein ( x i ) SEQUENCE DESCRIPTION: SEQ ID NO:12:

Gln  Val  Gln  Val  Val  Val  Val  Val  Phe  Gly  Ile
 1              5                        10

( 2 ) INFORMATION FOR SEQ ID NO:13:

( i ) SEQUENCE CHARACTERISTICS:
                    ( A ) LENGTH: 12 base pairs
                    ( B ) TYPE: nucleic acid
                    ( C ) STRANDEDNESS: single
                    ( D ) TOPOLOGY: linear ( i i ) MOLECULE TYPE: DNA (genomic)

( x i ) SEQUENCE DESCRIPTION: SEQ ID NO:13:

1 2
GGTACGTATA  CC ( 2 ) INFORMATION FOR SEQ ID NO:14:

( i ) SEQUENCE CHARACTERISTICS:
                    ( A ) LENGTH: 12 base pairs
                    ( B ) TYPE: nucleic acid
                    ( C ) STRANDEDNESS: single
                    ( D ) TOPOLOGY: linear ( i i ) MOLECULE TYPE: DNA (genomic)

( x i ) SEQUENCE DESCRIPTION: SEQ ID NO:14:

1 2
GGTATACGTA  CC ( 2 ) INFORMATION FOR SEQ ID NO:15:

( i ) SEQUENCE CHARACTERISTICS:
                    ( A ) LENGTH: 12 base pairs
                    ( B ) TYPE: nucleic acid
                    ( C ) STRANDEDNESS: single
                    ( D ) TOPOLOGY: linear ( i i ) MOLECULE TYPE: DNA (genomic)

( x i ) SEQUENCE DESCRIPTION: SEQ ID NO:15:

1 2
ACCTTGAGTA  CC ( 2 ) INFORMATION FOR SEQ ID NO:16:

( i ) SEQUENCE CHARACTERISTICS:
                    ( A ) LENGTH: 12 base pairs ( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:16:

GGTACTCAAG GT        12

( 2 ) INFORMATION FOR SEQ ID NO:17:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 6..38

( x i ) SEQUENCE DESCRIPTION: SEQ ID NO:17:

CTAGC TAT ACC AAA GAC ACC AAC AAC AAC TTG ACC TTG T        39
      Tyr Thr Lys Asp Thr Asn Asn Asn Leu Thr Leu
      1           5                   10

( 2 ) INFORMATION FOR SEQ ID NO:18:

( i ) SEQUENCE CHARACTERISTICS:
( A ) LENGTH: 11 amino acids
( B ) TYPE: amino acid
( D ) TOPOLOGY: linear ( i i ) MOLECULE TYPE: protein ( x i ) SEQUENCE DESCRIPTION: SEQ ID NO:18:

Tyr Thr Lys Asp Thr Asn Asn Asn Leu Thr Leu
1           5                   10

( 2 ) INFORMATION FOR SEQ ID NO:19:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 6..38

( x i ) SEQUENCE DESCRIPTION: SEQ ID NO:19:

CTAGA CAA GGT CAA GTT GTT GTT GGT GTC TTT GGT ATA G        39
      Gln Gly Gln Val Val Val Gly Val Phe Gly Ile
      1           5                   10

( 2 ) INFORMATION FOR SEQ ID NO:20:

( i ) SEQUENCE CHARACTERISTICS:
( A ) LENGTH: 11 amino acids
( B ) TYPE: amino acid
( D ) TOPOLOGY: linear ( i i ) MOLECULE TYPE: protein ( x i ) SEQUENCE DESCRIPTION: SEQ ID NO:20:

Gln Gly Gln Val Val Val Gly Val Phe Gly Ile ( 2 ) INFORMATION FOR SEQ ID NO:21:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:21:

ACTAGCTATA CC     12

( 2 ) INFORMATION FOR SEQ ID NO:22:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:22:

GGTATAGCTA GT     12

( 2 ) INFORMATION FOR SEQ ID NO:23:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:23:

ACCTTGTCTA GT     12

( 2 ) INFORMATION FOR SEQ ID NO:24:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:24:

ACTAGACAAG GT     12

( 2 ) INFORMATION FOR SEQ ID NO:25:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 2..16

( x i ) SEQUENCE DESCRIPTION: SEQ ID NO:25:

G GGC TGC AGC CTA AGT AC     18

```
Gly  Cys  Ser  Leu  Ser
 1                  5
```

( 2 ) INFORMATION FOR SEQ ID NO:26:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: protein ( x i ) SEQUENCE DESCRIPTION: SEQ ID NO:26:

```
Gly  Cys  Ser  Leu  Ser
 1                  5
```

( 2 ) INFORMATION FOR SEQ ID NO:27:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 5..13

( x i ) SEQUENCE DESCRIPTION: SEQ ID NO:27:

```
TTAG  GCT  GCA  GCC  CGTAC                                              18
      Ala  Ala  Ala
       1
```

( 2 ) INFORMATION FOR SEQ ID NO:28:

( i ) SEQUENCE CHARACTERISTICS:
        ( A ) LENGTH: 3 amino acids
        ( B ) TYPE: amino acid
        ( D ) TOPOLOGY: linear ( i i ) MOLECULE TYPE: protein ( x i ) SEQUENCE DESCRIPTION: SEQ ID NO:28:

```
Ala  Ala  Ala
 1
```

( 2 ) INFORMATION FOR SEQ ID NO:29:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:29:

```
GGGCTGCAGC CTAAGTAC                                                     18
```

( 2 ) INFORMATION FOR SEQ ID NO:30:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:30:

```
TTAGGCTGCA GCCCGTAC                                           1 8
```

IMMUNOGENIC MENINGOCOCCAL LPS AND OTHER MEMBRANE VESICLES AND VACCINE THEREFROM

The subject invention is directed at an immunity providing B cell activating molecule derived from a meningococcal lipopolysaccharide (LPS), said molecule comprising at least one epitope, said molecule comprising at least the common portion of the oligosaccharide portion (core region) of lipopolysaccharides which are specific for at least two meningococcal immunotypes. The invention is also directed at methods for the preparation thereof, both synthetically and through recombinant-DNA-techniques. Furthermore, the subject invention is directed at an outer membrane vesicle provided with a group of polypeptides which possess at least the immuo activity of outer membrane proteins (OMP's) bound to a membrane. The invention is also directed at a vaccine comprising such a molecule and/or such an outer membrane vesicle. A method for preparing such an outer membrane vesicle also falls within the scope of protection of the subject invention.

It is known that vaccines of purified capsular polysaccharides (CPS) can induce protective immunity. This immunity depends on the age of the vaccinated person and is only of a short duration. The intrinsic disadvantages of capsular polysaccharides as vaccines are circumvented by the classic approach of coupling capsular polysaccharides or oligosaccharides to be derived therefrom with proteins (Goebel, W. F., and O. T. Avery 1929 J. Exp. Med. 50:533–550 and Cruse, J. M. and R. E. Lewis (Ed.) 1989 Contrib. Microbiol. Immunol. Basel. Krager, 10:1–196). The coupling of polysaccharides to proteins results in changing the character of this type of antigen from thymus independent to thymus dependent. Such poly or oligosaccharide protein conjugates are in general very immunogenic in young children and can induce memory.

A number of examples of known saccharide peptide conjugates follow:

Conjugates of capsular polysaccharides (CPS) of *H. influenza b* with tetanus toxoid (TT) are known from the Dutch Patent Application 8602325.

Conjugates of capsular polysaccharides of meningococcal group A and C with tetanus toxoid were prepared, said conjugates appear to be very immunogenic in mice and rabbits ([Beuvery, E. C., A. Kaaden, V. Kanhai and A. B. Leussink, 1983. Physicochemical and immunological characterization of meningococcal group A and C polysaccharide-tetanus toxoid conjugates prepared by two methods. Vaccine 1:31–36], [Beuvery, E. C., F. Miedema, R. van Delft and K. Haverkamp, 1983. Preparation and immunochemical characterization of meningococcal group C polysaccharide tetanus toxoid conjugates as a new generation of vaccines. Infect. Immun. 40:39–45] and [Jennings, H. J. and H. C. Lugowski, 1981. Immunochemistry of groups A, B and C meningococcal polysaccharide-tetanus toxoid conjugates. J. Immunol. 127:1011–1018]).

Group B Meningococcus a bacteria group causing more than 50% of the cases of meningococcal disease in many countries is a group of bacteria whose capsular polysaccharides do not induce immune reaction or induce little immune reaction. (Poolman et al., The Lancet, September 1986, pages 555–558).

Therefore, a search has been carried out for the group B Meningococcus for the saccharide peptide conjugates that could be useful in a vaccine as capsular polysaccharides of this group do not give any immune reaction against gramnegative bacteria in test animals and human volunteers.

Therefore, saccharide peptide conjugates were made with modified capsular polysaccharide and carrier proteins ([Jennings, H. J., R. Roy, and A. Gamian, 1986. Induction of meningococcal group B polysaccharide-specific IgG antibodies in mice using an N-proprionylated B polysaccharide tetanus toxoid conjugate vaccine. J. Immunol. 137:1708–1713] and [Jennings, H. J. 1989. The capsular polysaccharide of group B *Neisseria meningitidis* as a vehicle for vaccine development. In Cruse, J. M., and R. E. Lewis, Conjugate Vaccines. Contrib. Microbiol. Immunol. Basel, Krager, 10:151–165]).

As it is suspected that anti group B antibodies (in particular IgG) demonstrate in vivo cross reaction with host antigens and as the use of a saccharide peptide conjugate comprising modified capsular polysaccharide of group B Meningococcus could therefore lead to causing auto immune disease most research is directed at a vaccine against group B Meningococcus is directed at the potential use of sub capsular components such as outer membrane proteins (OMP) and lipopolysaccharides (LPS).

So Jennings et al. describe conjugates of tetanus toxoid (TT) with dephosphorylated oligosaccharides (OS*) derived from meningococcal LPS. The immunogenicity of these OS*-TT conjugates was examined in rabbits (Infect. Immun. 43:407–412). Herein phosphoethanolamine was removed from the meningococcal oligosaccharides (OS) by treatment with hydrogen fluoride. The dephosphorylated oligosaccharides were subsequently coupled to tetanus toxoid. The thus obtained immunotype $L_3$ OS protein conjugate was only slightly immunogenic in rabbits which can probably be explained as a result of removal of the PEA group s.

In Infection and Immunity, March 1991, pages 843–851 Verheul et al. describe the preparation of meningococcal OS-protein conjugates with tetanus toxoid, wherein the phosphoethanolamine groups of the oligosaccharides have been maintained.

Oligosaccharides peptide conjugates, wherein saccharide portion and peptide portion originate from different organisms (mostly a tetanus or diptheria peptide) have the disdadvantage that oversensitivity or tolerance for said peptide portion (tetanus or diptheria carrier) can occur and can therefore lead to reduced response to the B cell activating part. Therefore, saccharide peptide conjugates provided with homologic carrier peptide have been searched for. Such a saccharide peptide conjugate will not only activate B cell memory but also reactivate T cell memory upon contact with the micro-organism in question.

Saccharide peptide conjugates are known comprising a homologous carrier peptide. Paton et al, describe conjugation of pneumolysine toxoid to type 19F capsular polysaccharide of *Streptococcus pneumoniae* (Infection and Immunity, July 1991, pages 2297–2304).

Saccharide peptide conjugates are also known comprising a homologous carrier peptide comprising a saccharide part derived from a lipopolysaccharide (LPS) of gram negative bacteria as immunity providing B cell activating part. Such a saccharide peptide conjugate offers as advantage the possibility to make a vaccine providing immunity against gramnegative bacteria, whose capsular polysaccharides provide no or insufficient immune reaction. A saccharide peptide conjugate comprising lipopolysaccharide as immunity providing B cell activating part also, however, has disadvantages. Lipopolysaccharide contains toxic parts and a saccharide peptide conjugate comprising a lipopolysaccharide with toxic parts will also be toxic.

In Contrib. Microbiol. Immunol. Basel, Karger, 1989, vol. 10, pages 166–189 Cryz. J. C. et al. describe vaccines against *Pseudomonas aeruginosa* comprising a saccharide peptide conjugate comprising detoxified lipopolysaccharide of *Pseudomonas aeruginosa* immunotype 5 which lipopolysaccharide is coupled to various carrier proteins. The carrier proteins can be both homologous and non-homologous. The carrier proteins mentioned in this article are tetanus toxoid, toxin A and pili of *Pseudomonas aeruginosa*.

The LPS of *Pseudomonas aeruginosa* is made harmless according to this article by removing ester bound fatty acids of Lipid A, so that the serologically active O polysaccharide portion can be incorporated in a saccharide peptide conjugate. Such detoxified LPA (D-LPS) was converted to an active ester by coupling to N-hydroxysuccinimide and subsequently the active ester was coupled to a protein which had been provided with a spacer (1,4-diaminobutane) in order to simplify the coupling. The D-LPS-TA-conjugate was not immunogenic however the D-LPS-pili-conjugate and the D-LPS-TT-conjugate were.

In an article by Boons et al. (Bioorganic and Medicinal Chemistry Letters, Vol. 1, No. 6, pages 303–308, 1991) it is described that a saccharide peptide conjugate (SPC) with two essential immunological domains (i.e. the B and T epitopes responsible for antibody specificity and T helper activity) which are covalently bound by means of an artificial spacer has been made as part of vaccine development with a broad action against *N. meningitidis*. In this known conjugate the B epitope function is provided by a fragment of the IC region of the LPS-immunotype 6 (IC=inner core). A T cell epitope comprising peptide is selected for inducing homologous T helper cell response (memory). The T cell epitope comprising peptide part of the known homologous SPC is the 47-59 part of a meningococcal OMP described by Wiertz E. J. H. J. et al (in Proceedings of the Eleventh American Peptide symposium, ed. River, J. E.; Marshall, G. R.; ESCOM, Leiden, 1990). Disadvantages of this known SPC are the necessary complicated and costly chemical synthesis on the one hand hindering production on a large scale for economic reasons and on the other hand the fact that only a part of the immuno action of OMP is used because only a small fragment of OMP comprising a T cell activating part is used, in respect of both B and T cell activating parts.

Until now it appeared impossible to couple a saccharide part to a complete OMP or a large OMP fragment comprising more than one epitope without changing the structure or composition which would lower the immuno activity of the OMP.

Furthermore, it is known that microorganisms producing OMP's incorporate these in their membrane in a certain configuration wherein portion of the OMP are anchored in the membrane and portions protrude in the shape of loops. The specific configuration is required for the immuo activity of the T cell activating parts present in the OMP. In NIPH ANNALS, Volume 14, number 2, December 1991 it is described by Frederiksen J. H. et al on pages 67–79 in particular on 69–71, that microorganisms can be treated in such a manner that they "bleb", i.e. form outer membrane vesicles (OMV's). Such outer membrane vesicles are provided with a very large number of OMP's on their surface and offer the possibility to be used as potent vaccine component as a large amount of OMP's are present in the conformation required for immuno activity. However, a number of the disadvantages of other vaccines comprising solely OMP a immuno activity activating component, are also valid for such a vaccine component. Known OMV vaccines appear to be able to provide intermediate protection in humans i.e. 50–80% protection.

The subject invention attempts to solve the problems that exist for the various known vaccine components. Firstly, the search has been directed at finding a B cell activating molecule that is small and simple to obtain, is not toxic and can also induce immunity against more than one LPS immuno type. The subject invention is also directed at an immunity providing B cell activating molecule derived from a meningococcal lipopolysaccharide (LPS), said molecule comprising at least one epitope, said molecule comprising at least the common part of the oligosaccharide part (core region) of lipopolysaccharides which are specific for at least two meningococcal immunotypes, preferably immunotypes L2 and L3 and wherein galactose is absent in the B cell activating part, as well as at derivatives of the molecule with immune reaction inducing capacity.

A suitable example of such a molecule is a molecule derived from the L2 core of a meningococcal LPS and having the following structure:

$$\begin{array}{c}\beta\text{-D-Glcp}(1\text{-}4)\text{-L-}\alpha\text{-D-Hepp-}(1\text{-}5)\text{-KDO}\\3\\|\\1\\\text{L-}\alpha\text{-D-Hepp3} < \text{- PEA}\\2\\|\\1\\\alpha\text{-D-GcNAc}\end{array}$$

Antibodies can be induced against such a structure which are specifically bactericidal for immunotypes L2 and L3, the most prevelent immunotypes. Another suitable example of such a molecule is a molecule derived from the L3 core and having the following structure:

$$\begin{array}{c}\beta\text{-D-Glcp}(1\text{-}4)\text{-L-}\alpha\text{-D-Hepp-}(1\text{-}5)\text{-KDO}\\3\\|\\1\\\alpha\text{-D-Glcp}(1\text{-}3)\text{-L-}\alpha\text{-D-Hepp6/7} < \text{- PEA}\\2\\|\\1\\\alpha\text{-D-GcNAc}\end{array}$$

This structure is also useful for inducing immune reaction against both immunotypes L2 and L3. Surprisingly, it has been found that an antibody which was known to exhibit cross reactivity for various meningococcal immunotypes, but about which it was unknown what structure it recognized can bind the two molecular structures as indicated above. The two molecular structures as indicated above differ from the epitopes postulated until now for L2 and L3 through the absence of galactose. The epitopes postulated to date are not completely necessary for inducing bactericidal antibodies with cross reactivity for various meningococcal immunotypes. The antibody used to illustrate this is mN8D6A and is described in Infection and Immunity, October 1988, pages 2631–2638 (by Kim, J. J., Mandrell, R. E., Zhen, H., Westerink, M. A. J., Poolman, J. T. and Griffiss, J. M.). In this article it is indicated that the antibody could bind to LPS to 28 group A *N.meningiditis* strains in dot blots and to multiple LOS components of various molecular weights obtained from the 28 strains in immunoblots.

Molecules according to the invention can form a part of saccharide peptide conjugates in the usual manner, wherein for example they are coupled to tetanus toxoid or to another known suitable carrier in vaccine technology. Advantageously a saccharide peptide conjugate comprising a molecule according to the invention also comprises a peptide part with at least one T helper cell activating epitope, which peptide part preferably comprises at least one homologous protein or a peptide fragment derived from a homologous protein, wherein homologous means that both B cell and T helper cell activating epitopes are derived from the same microorganisme. An outer membrane vesicle to which a saccharide peptide conjugate comprising a molecule according to the invention has been added or has been incorporated as B cell activating part is a suitable embodiment, said embodiment can be used advantageously in a vaccine. Preferably, an outer membrane vesicle to which a molecule or a saccharide peptide conjugate comprising such a molecule has been added, or in which such a molecule has been incorporated comprises class I OMP or class I OMP fragments as T helper cell activating part.

The subject invention is also directed at methods for preparing such lipopolysaccharide-derivatives according to the invention. Herefore, it is possible to apply mutagenesis, recombinant DNA techniques, enzymatic splitting or chemical synthesis. The method via recombinant DNA techniques comprises obtaining the molecule from a mutated or selected production strain producing at least LPS without galactose. For this a mutated meningococcal strain that does not produce galactose can be advantageously applied. In particular, a production strain can be applied that produces no or no functional galE anzym. In Proc. Natl. Acad. Sci. U.S.A. 86 (1989) pages 1669–1673 Frosch, M., Weisgerber, C. and Meyer, T. F. determined for *N.meningitidis* which part of the *N.meningitidis* genome comprises the genes for CPS production. This part was cloned on plasmid pMF32.35 and we found that this plasmid also comprises sequences encoding LPS biosynthesis. A meningococcal strain in which this plasmide has been integrated was deposited on Jul. 29, 1993 at CBS Baarn, the Netherlands, under number CBS 401.93. For an expert it is without a doubt via usual DNA techniques possible to apply one or more mutations or deletions in this part of meningococcal DNA to prevent galactose production. Specifically it is possible to apply one or more mutations or deletions in the cps locus that is present on this plasmid thereby preventing expression of any or any functional GalE. With probes comprising a part of the sequence encoding a part of the enzym GalE the location of the GalE gene can be determined simply and subsequently mutagenesis or deletion can be carried out in order to obtain a sequence expressing no or no functional GalE. The expression product of such a mutated cps locus will produce lipopolysaccharide without galactose. In the usual manner an expression vector can subsequently be made comprising such a mutated cps cassette or the relevant portion thereof. Now making a production strain with the aid of the mutated nucleotide sequence or the expression vector comprising such a sequence lies within the reach of an expert using typical protocols within the recombinant DNA technology. Advantageously a mutated meningococcal production strain in which a deletion in the wild type cps cassette has been made and which has been exchanged with a mutated cps cassette can be made in a simple manner.

Furthermore, the invention is directed at a solution to the problem of coupling OMP with a second component with immuno activity without damaging the immuno activity of the OMP, so that a vaccine component can be obtained comprising more than one T helper cell activating part. The subject invention is therefore directed at an outer membrane vesicle provided with polypeptides having at least the immuno activity of outer membrane proteins (OMP's) bound to a membrane, said outer membrane vesicle being characterized by the fact that the polypeptides are OMP's or OMP fragments anchored in the membrane with a mutation in one of the surface loops of the OMP from which the polypeptide has been derived. The invention is preferably directed at such an outer membrane vesicle, wherein the polypeptides are OMP's or OMP fragments anchored in the membrane with a mutation in one of the surface loops of the class 1 OMP from which the polypeptide has been derived. In particular, the invention is directed at such an outer membrane vesicle wherein the polypeptide comprises at least one mutation in one of the loops 2, 3, 5, 6, 7 or 8.

It has been found that applying mutations in these loops does not reduce the immuno activity of membrane bound class-1-OMP. Thereby the possibility to provide mutations at these locations enabling specific coupling of the OMP to another desired component, preferably a component with additional immuno activity at the position of the mutation is offered. An outer membrane vesicle according to the invention can be regarded as an outer membrane vesicle which has been activated for coupling.

The mutation is preferably located in one of the loops 6 or 7. These loops are located in the tertiary structure of the OMP at the most suitable positions with regard to loops 1 and 4, said loops comprising a number of important OMP epitopes.

The mutation can consist of at least the presence of an additional amino acid with a reactive side chain in one of the loops 2, 3, 5, 6, 7 or 8. This can be an insertion, deletion or substitution in one of the loops. A substitution is preferred as the natural situation is than most closely imitated. The form the mutation takes is not critical, however the location is.

As no cysteine is present in natural OMP and the sulfhydryl group is a good reactive group, this amino acid is preferably incorporated. Other amino acids such as lysine are possible, however the presence of such amino acids in the native OMP offers a number of reaction positions in the OMP for coupling and therefore the resulting SPV's will have to be screened in order to determine which have undergone the conjugation at the desired location. Incorporating protective groups will is most cases lead to complicated chemical reactions with a large risk of denaturation of the polypeptide.

As indicated the polypeptide can comprise complete OMP but also an OMP fragment. The OMP fragment should possess sufficient length and a structure such that it can be anchored in the membrane of a micro organism and possesses at least immuno activating activity, preferably as much as or more than the corresponding native OMP from which it has been derived. An OMV according to the invention which is preferred comprises a molecule according to the invention and/or a saccharide peptide conjugate comprising a molecule according to the invention.

An application of an OMV according to the invention is in production of a vaccine component that also comprises a conjugated saccharide part. The product of coupling a saccharide part to a polypeptide part of the outer membrane vesicle activated for coupling, an outer membrane vesicle (OMV) comprising a saccharide peptide conjugate (SPC), a so called saccharide peptide vesicle (SPV) will exhibit a broader immuno activity than the existing outer membrane vesicles comprising OMP. The SPV will therefore possess a larger and broader immuno activity then the known SPC's. A further advantage is that the natural activity by which a micro organism anchors OMP's in the membrane can in an economical and simple fashion be used to produce a vaccine component with broader and stronger immuno activity. The subject invention is directed at an SPV such as has been described.

The coupling of a peptide part of an activated outer membrane vesicle to a saccharide part, said saccharide part comprising at least an immunity providing B cell activating part with at least one epitope derived from a lipopolysaccharide (LPS) of a gramnegative bacteria and an outer membrane vesicle comprising a fragment of a B cell activating part with at least one epitope isolated from a gramnegative bacteria is preferred. The invention also comprises a SPV provided with polypeptides having at least the immuno activity of OMP, said polypeptides forming a part of saccharide peptide conjugates, wherein the saccharide part and the peptide part of such a conjugate are coupled at the location of the mutation in one of the loops 2, 3, 4, 5, 6, 7 or 8 of the polypeptide.

A SPV comprising the LPS "core region" or a fragment derived therefrom as B cell activating part of the saccharide part will be safer as component of a vaccine than a SPV comprising a saccharide peptide conjugate comprising native LPS due to the absence of the toxic parts. Moreover, such a "core" containing saccharide peptide conjugate has the advantage that it can contain a large number of different LPS "core" B cell activating parts than a SPC with native LPS that becomes toxic, when too much of the toxic component lipid A is incorporated.

Meningococcal lipopolysaccharide is toxic and comprises three parts. In FIG. 1 a meningococcal LPS is illustrated. The lipid A part is toxic and the lacto-N-neotetraose unit can perhaps lead to induction of auto antibodies. The oligosaccharide part of meningococcal LPS, that so called "core region" is not toxic. The so called "inner core region" is the part of the "core region" of the oligosaccharide part of meningococcal LPS in which the lacto-N-neotetraose unit is absent. A saccharide peptide conjugate comprising a B cell activating part, comprising the "core" oligosaccharide of *Meningococcus* or a fragment derived therefrom is a suitable example of a SPC that can be a part of a SPV according to the invention.

Indeed, a saccharide peptide conjugate comprising a saccharide part derived from *Meningococcus* lacking toxic lipid A and also lacking the complete lacto-N-neotetraose unit has been described by Boons et al, however, in this known vaccine component the saccharide part is coupled to a fragment derived from OMP comprising only one T cell epitope and the SPC does not form a part of an outer membrane vesicle.

For a SPV according to the invention native LPS to be applied can be isolated and subsequently lipid A and a part of the tetraose unit can be removed. Meningococcal lipopolysaccharide (LPS) can for example be isolated by the extraction method with hot water and phenol of Westphal (Westphal, O. and Jann. J. K., 1965, Methods Carbohydr. Chem. 5. 83–91). In short LPS is hydrolysed in 1% acetic acid unit flocculation occurs. Lipid A is removed by centrifugation and the oligosaccharides are purified over a Biogel column. Subsequently, the major oligosaccharide can be coupled to the peptide part.

"Core" oligosaccharide or an operative derivative thereof obtained by such a method can be incorporated in a saccharide peptide vesicle according to the invention.

As obtaining a B cell activating part derived from native LPS is a tedious process and as complete purification of the "core" oligosaccharide is also problematic the B cell activating part of the saccharide part of a saccharide peptide vesicle according to the invention can be synthesized. A saccharide peptide vesicle according to the invention can therefore comprises a synthetic B cell activating part in the saccharide part.

It is also possible to obtain a non toxic B cell activating part of the SPV derived from an LPS via a biochemical route, such as mutagenesis or enzymatic splitting. This route is possible if via molecular biological methods a production strain is made that is capable of producing an altered lipid A and/or lacto-N-neotetraose. In any case, the terminal galactose of the lacto-N-tetraose will have to be removed and a mutant production strain that does not produce galactose for incorporation in LPS can be made in a simple manner, as has been indicated for the preparation of a molecule according to the invention above. In particular the subject invention is also directed at an SPV in the various embodiments that have already been extolled, wherein the saccharide part comprises an immunity providing B cell activating molecule with at least one epitope derived from a meningococcal lipopolysaccharide (LPS) said molecule comprising at least the communal part of the oligosaccharide part (core region) of lipopolysaccharides which are specific for at least two meningococcal immunotypes preferably immunotypes L2 and L3 and wherein galactose is absent from the B cell activating part, as well as derivatives of the molecule having immune reaction inducing capacity.

The saccharide peptide vesicles according to the invention can be conjugated by a spacer. This provides the advantage that no intramolecular reactions occur between the reactive groups of the saccharide part and the peptide part. Such reactions can namely lead to an altered tertiary structure of the saccharide part and/or peptide part resulting in deterioration of immuno activity.

A number of LPS immunotype specific epitopes owe their activity to the presence of at least one phosphoethanolamine (PEA) group. Therefore, a saccharide peptide vesicle according to the invention is preferred wherein PEA group s of the B cell activating part of the saccharide part comprise free amino groups. An example of such a saccharide peptide vesicle according to the invention comprising an immuno specific B cell activating part in the saccharide part, is a saccharide peptide vesicle comprising LPS of meningococcus with immunotype $L_3$ in the saccharide part. Such a saccharide peptide vesicle comprising an immuno specific epitope of immunotype $L_3$ will preferably comprise a B cell activating part with PEA group s having free amino groups.

Saccharide peptide vesicles according to the invention advantageously comprise a saccharide part comprising a B cell activating part that can give cross section with more than one immunotype. A vaccine comprising such a saccharide peptide vesicle according to the invention wil provide protection against more than one immunotype.

At the moment twelve different lipopolysaccharides are known for meningococcal strains (which corresponds to 12 immunotypes). The differences in the meningococcal LPS immunotypes have been localized in the oligosaccharide part of the LPS ("core region"). Recently the complete primary structures of the oligosaccharides for immunotypes $L_1$, $L2$, $L_3$, $L_5$ and $L_6$ were postulated; these are illustrated in FIG. 2 (Difabio J. L. et al. 1990, Structure of the L1 and L6 core oligosaccharide of *Neisseria meningitidis*, Can. J. Chem. 86:1029–1034; Jennings, H. J. et al, 1987, Structure and Immunochemistry of meningococcal lipopolysaccharides, Anthonie van Leeuwenhoek 53:519–522; Michon, F. et al, 1990, Structure of the L5 lipopolysaccharide core oligosaccharide of *Neisseria meningitidis*, J. Biol. Chem. 256:7243–7247; Verhuel, A. F. M. et al Infection and Immunity (1991), 51: p 3566–3573).

A saccharide peptide vesicle according to the invention comprising one or more oligosaccharides is useful as component of a vaccine directed against at least one meningococcal immunotype. A saccharide peptide vesicle according to the invention according at least the B cell activating part of at least one of the oligosaccharides in said saccharide part can therefore advantageously be used as component of a vaccine directed against at least one meningococcal immunotype.

The oligosaccharides of the immunotypes differ with regard to monosaccharide composition, amount and location of phosphoethanolamine (PEA) groups and the degree of acetylation of the α(1→2) bound GlCNAc-unit or other units. For most immunotypes the basic structure of the oligosaccharide "core" is the same.

As the "core" oligosaccharides of meningococcal LPS exhibit conformity for various immunotypes the "core" comprises more than one immunotype specific epitope. A SPV according to the invention that comprises such a "core" as B cell activating part of the saccharide part will be preferred. Such a SPV according to the invention can have a simultaneous B cell activating effect on a number of different immunotypes. A saccharide peptide vesicle according to the invention that can have a simultaneous B cell activating effect for a number of immunotypes can also comprise a derived fragment comprising more than one immunotype specific epitope.

It is also possible to incorporate only a relevant portion of the "core" oligosaccharide as fragment in a SPV according to the invention, providing specific immunity for specific immunotype. It is also possible to incorporate more than one B cell activating part in the saccharide part of a SPV according to the invention so that such a SPV comprises various specific immunity providing parts and can therefore provide immunity for various specific immunotypes.

B cell activating parts of the saccharide part with specific immunity providing action against various immunotypes or B cell activating parts of the saccharide part having cross reactive immunity providing action can advantageously be incorporated in the saccharide part of a saccharide peptide vesicle according to the invention. It has become possible to synthesize well defined oligosaccharides with increasing complexity and molecular weight, so that oligosaccharides comprising one or more B cell activating structures can be synthesized.

It is known about *Meningococcus* that immunotypes L3 and L2 cause approx. 70% and 30% respectively of group B *Meningococcal meningitis*. Therefore, saccharide peptide vesicles according to the invention comprising at least B cell activating parts of L3 and/or L2 immunotypes in the saccharide part of the saccharide peptide vesicle are preferred.

A saccharide peptide vesicle according to the invention comprising at least a B cell activating part of the saccharide part that is a derivative of

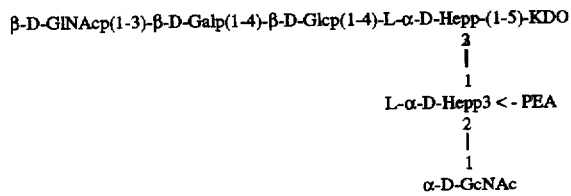

or

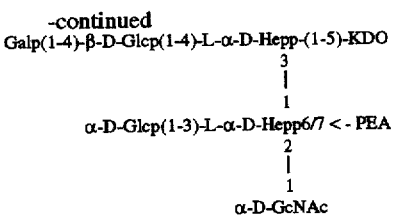

A saccharide peptide vesicle that is preferred is a SPV comprising a B cell activating part in the saccharide part exhibiting at least cross reaction with two immunotypes of gram negative bacteria. An example of such a saccharide peptide vesicle exhibits at least cross reaction with meningococcal immunotypes L2 and L3. Such a saccharide peptide vesicle therefore comprises a molecule with structure

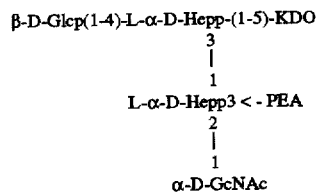

and/or

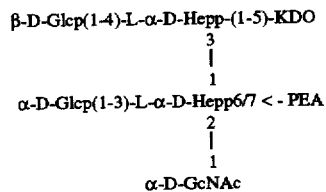

A saccharide peptide vesicle that is also preferred is a SPV comprising a B cell activating part in the saccharide part exhibiting at least cross reaction with meningococcus immunotypes L1 and L3.

A saccharide peptide vesicle which exhibits cross reaction with at least immunotypes $L_1$, $L_2$ and $L_3$ comprises at least the branched oligosaccharide β-D-Glcp(1→4)-[L-α-D-Hepp(1→3)]-L-α-D-Hepp) as B cell activating part in the saccharide part. A suitable example of such a saccharide peptide vesicle according to the invention also comprises a PEA group on the 0–3 of the heptosylunit of the branched oligosaccharide β-D-Glcp(1→4)-[L-α-D-Hepp(1→3)]-$_L$-α-D-Hepp).

A saccharide peptide vesicle according to the invention exhibiting cross reaction with more immunotypes than $L_1$, $L_2$ and $L_3$ comprises at least the branched oligosaccharide β-D-Glcp(1→4)-[L-α-D-Hepp(1→3)]-L-α-Hepp) provided with a spacer giving a link with at least one another immunotype specific B cell activating part with at least one epitope as B cell activating part in the saccharide part.

A SPV according to the invention can comprise a saccharide part that is synthesized and/or modified with regard to a natural B cell activating part as B cell activating part for a certain immunotype. Such a synthesized and/or modified B cell activating part will preferably exhibit cross reaction with various immunotypes and/or give an improved immune reaction with regard to the corresponding part of the natural LPS. In any case the terminal galactose should be removed, either via enzymatic route, or via genetic manipulation, through mutation. As has been indicated above the complete absence of galactose in such structures is a possible embodiment, which is obtainable by a person skilled in the art through recombinant DNA technology.

Such a synthesized and/or modified B cell activating part can arise through selective addition and/or deletion of certain groups and/or sugar units.

A saccharide peptide vesicle according to the invention will preferably comprise an outer membrane proteine (OMP) or a fragment derived from an OMP as peptide part. Preferably, a SPV according to the invention will comprise an OMP of Meningococcus class I as this OMP can induce protective antibodies, does not possess a tendency to block antibodies against other proteins and does not exhibit too great an antigenic variation. Many recognition sites for human T cells have been researched on the class I outer membrane protein of Meningococcus H44/76, making it a suitable starting strain for OMP to be used.

The subject patent application is also directed at a method for preparing an outer membrane vesicle according to the invention. This method comprises the following steps
1) a nucleotide sequence encoding the polypeptide is expressed in a bacteria;
2) the bacteria is cultivated under known circumstances for producing outer membrane vesicles as is described in NIPH ANNALS, Volume 14, number 2, December 1991 by Fredriksen J. H. et al on p 67–79, in particular on page 69–71 and the thus created membrane pieces with polypeptide can optionally be isolated.

For preparing a SPV according to the invention subsequently
3) the membrane pieces formed in step 2 can be provided with saccharide peptide conjugates by coupling the polypeptide to the desired saccharide part.

For preparing an OMV or a SPV according to the invention the required nucleotide sequence for step 1) to be used can be a recombinant nucleotide sequence encoding a class I OMP or a fragment thereof with at least the immuno activity of class I OMP, in which in comparison to the corresponding natural sequence a mutation has been created in one of the surface loops. A mutation in one of the loops 2, 3, 4, 5, 6, 7 or 8 in particular in loops 6 and 7 is preferred. The mutation results in a codon for at least one amino acid having a specific reactive side in one of the surface loops. In particular the mutation results in a codon for cysteine. A saccharide part obtained by recombinant DNA technology or via a synthetic route can be used in the method for preparing a SPV according to the invention. In particular a molecule according to the invention which is obtainable as has been described herein elsewhere can be used as saccharide part.

For coupling a saccharide part to an OMV according the invention in particular to an OMV-SH provided with a cysteine group the following reaction schedule can be followed:

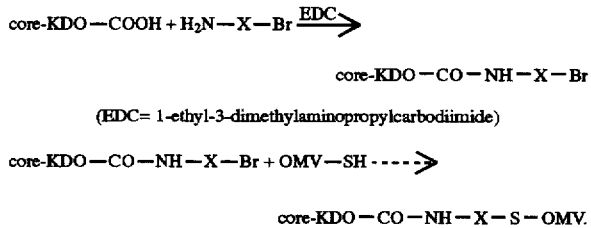

More specifically the reaction can be executed as follows:
BrCH$_2$—CO—NH—(CH$_2$)$_4$—NH$_2$ (substance 1, excess)+ OS-KDO+EDC+sulfo-NSH—$^{pH8}$ OS———CO—CH$_2$Br (substance 2). Substance 2 is subjected to gel filtration and subsequently substance 2+OMV-SH→conjugate.

Another possibility for executing the coupling is with BrCH$_2$—CO—NH—(CH$_2$)$_4$—NH—CO—CH$_2$Br (substance 3, excess)+OS-SH (as described on pages 34 and 35 of Andre Verhuel's thesis, Meningococcal LPS derived oligosaccharide protein conjugate vaccines Oct. 29, 1991, Utrecht). This results in OS———CO—CH$_2$Br (substance 2*). This is subjected to gelfiltration or optionally to a simple ET$_{20}$-rinse. Substance 2* can subsequently be converted to the conjugate with OMV-SH. As substance 3 is lipophilic the modification of OS-SH occurs in a mixture of an aqueous buffer and an organic solvent, such as dioxane. For this reason the reaction of OMV-SH with substance 3 followed after purification by incubation with OS-SH is less attractive.

For specific coupling of carbohydrates the presence of suitable groups such as an amino (—NH$_2$), carboxylic acid (—COOH), thiol (—SH) or an aldehyde (CHO) is necessary within the carbohydrate antigen (Dick, W. E. et al., 1989, Glycoconjugates of bacterial carbohydrate antigens. In Cruse, J. M. and R. E. Lewis, Conjugate vaccines, Contrib. Microbiol. Immunol., Basel, Krager, 10:48–114). These groups can be present in the antigen but must often be incorporated via chemical or enzymatic methods. It is preferred to use a coupling method resulting in as small a modification of the carbohydrate and protein antigen as possible. The use of a specific spacer to be incorporated is conducive for this. It is preferred to destroy the epitope or epitopes present or to generate undesired immuno dominant neo antigens as little as possible. The influence of the coupling method on the immunologic characteristics of an oligosaccharide-peptide vesicle is large is small oligosaccharides are used (Hoppner, W., et al., 1985, Study on the carbohydrate specificity of antibodies formed in rabbits to synthetic glycoprotein with the carbohydrate structure of asialoglycophorin A. Mol. Immunol. 12:1341–1348).

Most known vaccines are based on capsular polysaccharides or O antigens consisting of repetitive units of 1 to 8 monosaccharides, in order to minimalise the influence of the coupling by use of larger oligosaccharides. Meningococcal LPS does not contain repetitive units and therefore the selection of the coupling method using meningococcal LPS will in particular be important for the immunologic and immunochemical characteristics of the resulting conjugate.

Preferably the saccharide is coupled to the peptide via a spacer containing the terminal reactive groups such as NH$_2$ and COOH. The use of a spacer in saccharide peptide vesicles according to the invention has the advantage that the tertiary structure of the saccharide part is not altered, which is important for the immuno activity of the saccharide.

In the meningococcal oligosaccharides two groups are available for use in coupling such an oligosaccharide to a carrier peptide: the free amino group of the phosphoethanolamine group (PEA group) and the carboxylic acid group of the KDO unit. The PEA group should preferably not be used for coupling as this group probably comprises part of a number of the immunotype specific epitopes. Therefore, it is preferable in a saccharide peptide vesicle according to the invention to maintain phosphoethanolamine groups with free amino groups. Typically saccharide peptide conjugates can be made on the basis of coupling the carboxylic acid group of the oligosaccharide to the free amino groups of the peptide. When this method is applied with the meningococcal oligosaccharide this can result in coupling of oligosaccharide to oligosaccharide or of oligosaccharide to carboxylic acid groups of the peptide by the PEA group of the oligosaccharide. Jennings et al. (Infect. Immun. 43:407–412) have solved this problem by removing the PEA groups through treatment with hydrogen fluoride. The dephosphorylated oligosaccharides were subsequently coupled to tetanus toxoid by incorporating β-(4-aminophenyl)ethylamine as spacer at the reducing terminus via reductive amination (which lead to loss of the ring structure of KDO), followed by activation of the amino group with thiophosgen followed by coupling to tetanus toxoid. Such conjugates with immunotype $L_2$, $L_5$ and $_L10$ were very immunogenic in rabbits whereas those of $L_3$ were badly immunogenic. For this last group the loss of PEA group s and/or ring structure of the KDO group appears to be important for the immunity and it is preferable to make a saccharide peptide vesicle with $L_3$ oligosaccharide of Meningococcus with the PEA group s and the KDO ring structure of the meningococcal oligosaccharide have been modified as little as possible.

The abovementioned methods do not suffice for preparing a saccharide peptide vesicle according to the invention in which the B cell activating activity of the saccharide part depends on the presence of one or more phosphoethanol (PEA) groups. Additional measures are necessary for preparing such saccharide peptide vesicles.

A possibility for preparation of a saccharide peptide vesicle according to the invention that solves the abovementioned problem is used of a saccharide part that has been synthetically obtained.

With current techniques it is possible to synthesize oligosaccharides. Furthermore, as has been described previously in this subject pattern application, in the case of saccharide peptide vesicles comprising oligosaccharides derived from LPS it can be advantageous to synthesize the B cell activating part that is present in the "inner core" of LPS. Another advantage of a synthetically obtained saccharide part lies in the possibility to incorporate the minimum saccharide that operates as B cell activating part in the SPC according to the invention. Furthermore, it is also possible to synthesize a saccharide part comprising a minimum oligosaccharide with cross reactivity immunity providing activity. It is also possible to synthesize B cell activating parts providing better immuno activity than the natural oligosaccharides.

It is simpler to place the spacer at a specific location with a synthetically obtained saccharide part. It is also possible to incorporate one or more phosphoethanol groups in the B cell activating part of the saccharide part for obtaining improved immuno activity.

In order to place the spacer at a specific location in the saccharide it is preferred to provide the reactive groups of the saccharide with protective groups before the spacer is coupled. The reactive group at which the coupling with the spacer occurs is not provided with a protective group. This method prevents groups which are essential for the immunity providing activity to be removed or altered during coupling of the spacer.

The invention is also directed at a nucleotide sequence encoding recombinant OMP or a recombinant OMP fragment which is discernible from non recombinant OMP or a non OMP fragment by at least a mutation in one of the loops 2, 3, 6, 7 or 8 of the OMP. In particular the invention is directed at such a nucleotide sequence with a mutation in one of the loops 6 or 7. A sequence also including the most important antigenic determinants located in loops 1 and 4 is preferred. The nucleotide sequence can comprise an insertion, deletion or alteration of at least one codon as mutation, with a preference for a mutation leading to at least formation of a codon including an additional amino acid with a reactive side group in one of the loops 2, 3, 6, 7 or 8 in comparison to the amino acid sequence of the corresponding OMP or OMP fragment. The nucleotide sequence according to the invention further preferably comprises a codon encoding cysteine.

The invention is also directed at an expression vector comprising the nucleotide sequence for OMP or an OMP fragment according to the invention as well as a micro organism comprising said nucleotide sequence and/or said expression vector according to the invention.

The invention is also directed at a polypeptide having at least the immuno activity of OMP, which polypeptide is characterized by the presence of an additional amino acid with a reactive side chain in one of the surface loops, in particular loops 2, 3, 5, 6, 7 or 8, in comparison with corresponding native OMP or a corresponding fragment of the native OMP. A polypeptide with an amino acid with a specific reactive side chain in loop 6 or 7 is preferred because these loops will be of least hindrance to the tertiary structure of OMP of loops 1 and 4 when a saccharide part is coupled. Preferably a polypeptide according to the invention comprises a cysteine as amino acid. As native OMP does not comprise cysteine it is in a polypeptide according to the invention possible to couple very specifically to cysteine. The incorporation of an additional lysine is also one of the possibilities, however, it is not preferred due to the presence of more than one lysine in native OMP and therefore also in the polypeptide. The coupling will therefore provide more than one conjugate and will require screening for the correct conjugate.

A saccharide peptide conjugate comprising at least one epitope of an OMP characterized by the presence of a polypeptide according to the invention also falls within the scope of the invention, as does a vaccine comprising an outer membrane vesicle, a SPV, a polypeptide or a saccharide peptide conjugate according to the invention in an effective amount.

Furthermore, the invention is directed at a nucleotide sequence comprising meningococcal LPS encoding material, said nucleotide sequence being discernible from the wild type nucleotide sequence by at least one mutation or deletion whereby the expression product of the mutated nucleotide sequence does not comprise any or does not comprise functional GalE in contrast to the nucleotide sequence of the wild type. Such a nucleotide sequence can comprise a mutation in the cps locus of meningococcal DNA or equivalent DNA derived therefrom, for example in DNA derived from *N.meningiditis* such as on plasmid pMF32.25 which has been integrated in meningococcal strain CBS 401.93 and deposited at the CBS in Baarn on Jul. 29, 1993. Preferably such a sequence comprises a mutation in the D or E region. An expression vector comprising a nucleotide sequence of LPS meningococcal encoding material according to the invention, as well as a microorganism comprising such a nucleotide sequence and capable of expressing such a sequence fall within the scope of the subject invention. In particular, a mutagenised meningococcal strain that produces LPS without containing galactose falls within the scope of the subject invention as does a vaccine comprising such a micro organism or molecule according to the invention.

EXAMPLE I

Summary

Class 1 outer membrane proteins are used for vaccine development against B Meningococci. These proteins naturally contain two variable areas (=epitopes), which bind bactericidal antibodies. These epitopes are located in two loops 1 and 4 that are exposed at the surface. Four meningococcal strains were made with extra epitopes in loops 5 and 6 of class 1 protein (see table A), from which it is apparent that insertion at loops 5 and 6 is possible without disadvantages to epitopes in 1 and 4. The strains all have the natural epitopes of the parent strain A8-6[r] in loops 1 and 4, namely the P1.5 and P1.2 epitopes. Furthermore, strain J007 has an extra P1.7 and strain J016 has an extra P1.16 epitope, whereas strain J716 has two extra epitopes, the P1.7 and the P1.16 in loop 6. Finally, strain P106 has an extra P1.16 epitope in loop 5. All these strains are capable of binding monoclonal antibodies to the cell surface.

TABLE A

| *meningococcal* string | loop 1 | loop 4 | loop 5 | loop 6 |
|---|---|---|---|---|
| J007 | P1.5 | P1.2 | | P1.7 |
| J016 | P1.5 | P1.2 | | P1.16 |
| J716 | P1.5 | P1.2 | | P1.7 + P1.16 |
| P016 | P1.5 | P1.2 | P1.16 | |

With the aid of this information new meningococcal strains can be produced containing mutations in OMP which strains can be used to produce outer membrane vesicles (=OMV's) consisting of pieces of outer membrane and are under certain circumstances secreted by *N. meningitidis*. These pieces can subsequently be coupled to LPS. The OMV's can serve as vaccine against B Meningococci.

1.1 The structure of the class 1 OMP

The class 1 OMP's are cation selective pore proteins [15]. The protein is approx. 374 amino acids long and is preceeded by a signal peptide of 19 amino acids [1]. A model for the topology of the protein in the outer membrane predicts eight loops exposed at the surface.

The transmembrane sequences have been maintained between the various *Neisseria* porins and form a β sheet structure. The hydrophilic exposed loops at the surface exhibit large variation in length and sequence. When the different class 1 OMP's are compared, the sequences exhibit a homology of 90%. The variation in the sequences appears to be located in the first and the fourth loop. These are referred to as variable regions or epitopes. Bacterial antibodies appeared to bind the epitopes in loops 1 and 4, which corresponds to the fact that these loops are the longest. These two epitopes determine the subtype specificity of the class 1 OMP [6].

1.2 Incorporation of extra epitopes in the meningococcal class 1 OMP

When the different epitopes of the class 1 OMP's are compared, in total 10 different subtype specific epitopes can be discerned. Oligonucleotides with "sticky ends" are synthesized for two epitopes, the P1.7 and P1.16. These oligonucleotides were subsequently placed in loop 5 and loop 6 of the class 1 OMP gene.

The incorporation of the P1.7 and P1.16 oligonucleotides in the class 1 OMP gene provided new strains with extra epitopes in the class 1 OMP. These strains already comprise the P1.5 epitope in loop 1 and the P1.2 epitope in loop 4. The newly incorporated epitopes, P1.7 and P1.16 have been placed in loop 5 or 6. The expression of the incorporated epitopes in the new strains has subsequently been observed with whole cell ELISA and compared to the expression of the parent strain. Subsequently the outer membrane complexes (OMC's) have been isolated from both the new strains and the parent strain which are used for the immunisation of mice.

1.3 Materials

The used DNA & plasmid:

The plasmid pTZ19R is a plasmid derived from Pharmacia, encoding for a.o. Amp-resistance (Ampr) and the lac Z'-gene. The used plasmid 2-2ΔSE is a derivative of pTZ19R. This plasmid contains a 1.9 kB insert with a part of the class 1 OMP gene from meningococcal strain 2996 (P1.5,2), from amino acid 100. This insert is located at the EcoRI site of the Multiple Cloning Site (=MCS) of pTZ19R. Through a deletion in the Multiple Cloning Site from the SalI site of the EcoRI site (where the insert begins), the class 1 gene has come into the same reading frame as the lac Z' derivative of pTZ19R. The class I OMP gene in this plasmid contains a KpnI restriction site in loop 5.

Another used plasmid pPH204 is again a derivative of 2-2ΔSE.

The class 1 OMP gene in this plasmid contains a new KpnI restriction site, namely in loop 6 instead of loop 5. The original KpnI site in loop 5 has been replaced by a BamHI restriction site and subsequently a KpnI site has been made in loop 6 by PCR mutagenesis [17].

The used enzymes:

The used enzymes are all derived from Boehringer Mannheim, together with the supplied buffers.

KpnI (vol. act.: 10 U/μl), with incubation buffer L.

SpeI (vol. act.: 10 U/μl), with incubation buffer H.

Sna BI (vol. act.: 8 U/μl), with incubation buffer M.

T4 DNA ligase (vol. act.: 1 U/μl), with T4 DNA ligase buffer.

With corresponding incubation buffers:

M buffer (1×): 10 mM Tris-HCl; 10 mM $MgCl_2$; 50 mM NaCl; 1 mM dithioerythritol (DTE), pH 7.5 (at 37° C.)

L buffer (1×): 10 mM Tris-HCl; 10 mM $MgCl_2$; 1 mM dithioerythritol (DTE), pH 7.5 (at 37° C.)

H buffer (1×): 50 mM Tris-HCl; 10 mM $MgCl_2$; 100 mM NaCl; 1 mM dithioerythritol (DTE) pH 7.5 (at 37° C.)

T4 DNA ligase buffer (10×): 660 mM Tris-HCl; 50 mM $MgCl_2$; 50 mM dithioerythritol; 10 mM ATP; pH 7.5 (at 37° C.)

The used monoclonal antibodies directed at the epitopes and LPS-types:

TABLE B

| monoclonal or LPS-type | type, subtype | |
|---|---|---|
| MN16C13F4 | P1.2 | P1 subtype specific |
| MN22.19A9 | P1.5 | |
| MN14C11.6 | P1.7 | |
| MN5C11G | P1.16 | LPS immunotype |
| MN14F21.11 | L1 | specific |
| 4A8B2 | L3(7.9) | |
| 4D1-B3 | L3(7.9) | |
| MN3A8C | L5 | |
| MN4C1B | L6(4.9) | |
| MNA11G | L11,12 | |
| MN9C10D | L8,10,11,12 | |
| 3A12-E1 | L3,7,8,9 | |
| MN15A17F12 | L9, 10 | |
| MN15A8-1 | Lipid A | | all monoclonals derived from RIVM.

The other materials are mentioned in the methods (1.4).

The used bacterial strains:
E. coliK12 (NM522: This bacteria strain is Hsd⁻ (=does not contain restriction modification system)
meningococcal strain H44/76 B⁻ (P1.7,1): This bacteria strain is a capsule deficient class 3 deficient mutant of H44/76 (P1.7,16).
meningococcal strain A8-6' B⁻ (P1.5,2): This bacteria strain is a capsule deficient mutant H44/77 (P1.7,16), which has been transformed with the class 1 protein of 2996 (P1.5,2) [17].

1.4 Methods 1.4.1 Control of pPH204 through transformation to Meningococci.

The constructed plasmid pPH204 (P1.2) has been transformed to meningococcal strain H44/76 B⁻ (P1.7,16). Here the P1.16 epitope in loop 4 of H44/76 B⁻ was exchanged with the P1.2 epitope of plasmid pPH204. With the aid of colony blotting and immunoblotting (see further) P1.2⁺ colonies were isolated providing the strain J072 after control with SDS-PAGE, Western- and immunoblotting, see also table B in Results (1.5).

1.4.2. Incorporation of extra epitopes in meningococcal class 1 OMP 1.4.2.1 Incorporation of oligonucleotides in the plasmids pPH204 and 2-2ΔSE The used class 1 OMP gene in plasmid pPH204 contains a restriction site for KpnI in the part encoding loop 6. An oligonucleotide with KpnI sticky ends which encodes the P1.7 epitope as indicated below and in preparation & insertion of oligonucleotides (1.4.3) was placed herein. Through incorporation of the oligonucleotide the KpnI restriction site disappeared and a unique SpeI restriction site was created. This plasmid is named construct pJB007.

2.1 oligonucleotide of the P1.7 epitope with KpnI sticky ends (SEQ ID NOS:1–4)

Upon insertion of the oligonucleotide in the plasmid, KpnI site disappears and a unique SpeI site appears:

| left (SEQ ID NO:5 and 6): | right (SEQ ID NOS:7 and 8): |
|---|---|
| 5'-GGTACGIAAC GGC-3' | 5'-GTT ACTIAGTACC-3' |
| 3'-CCATGCITTG CCG-5' | 3'-CAA TGAITCATGG-5' |

In the same manner an oligonucleotide with KpnI sticky ends was placed in loop 6 encoding the P1.16 epitope as indicated below and in preparation & insertion of oligonucleotides (1.4.3). Through incorporation of the oligonucleotide the KpnI restriction site also disappeared here, however a unique SnaBI restriction site was created. This plasmid is named construct pJB016.

2.2 oligonucleotide of the P1.16 epitope with KpnI sticky ends (SEQ ID NOS:9 and 10)

```
        Y   T   K   D   T   N   N   N   L   T   L
5'-GITAT ACC AAA GAC ACC AAC AAC AAC TTG ACC TTGIAGTAC-3'
3'-CATGCIATA TGG TTT CTG TTG TTG TTG AAC TTG AACIT-5'
        I   G   F   V   G   V   V   V   Q   G   Q
```

| restriction enzyme: | restriction enzyme: |
|---|---|
| TAC/GTA | GGTAC/C |
| ATG/CAT | C/CATGG |
| SnaBI | KpnI |

From insertion of the oligonucleotide in the plasmid, KpnI site disappears and a unique SnaBI site appears:

| left (SEQ ID NOS:13 and 14): | right (SEQ ID NOS:15 and 16): |
|---|---|
| 5'-GGTACGITAT ACC-3' | 5'-ACC TTGIAGTACC-3' |
| 3'-CCATGCIATA TGG-5' | 3'-TGG AACITCATGG-5' |

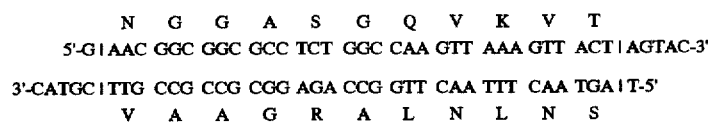

```
        N   G   G   A   S   G   Q   V   K   V   T
5'-GIAAC GGC GGC GCC TCT GGC CAA GTT AAA GTT ACTIAGTAC-3'
3'-CATGCITTG CCG CCG CGG AGA CCG GTT CAA TTT CAA TGAIT-5'
        V   A   A   G   R   A   L   N   L   N   S
```

| restriction enzym: | restriction enzym: |
|---|---|
| A/CTACT | GGTAC/C |
| TGATC/A | C/CATGG |
| SpeI | KpnI |

Subsequently an oligonucleotide with SpeI sticky ends behind the oligonucleotide P1.7 was placed in loop 6 in the construct pJB007, whereby the oligo encodes the P1.16 epitope as illustrated below. Hereby the SpeI restriction site disappeared through incorporation of the oligonucleotide. This plasmid is named construct pJB716.

2.3 oligonucleotide of the P1.16 epitope with SpeI sticky ends (SEQ ID NOS:17–20)

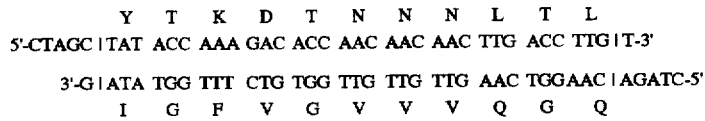

```
       Y   T   K   D   T   N   N   N   L   T   L
5'-CTAGC|TAT ACC AAA GAC ACC AAC AAC AAC TTG ACC TTG|T-3'

3'-G|ATA TGG TTT CTG TGG TTG TTG TTG AAC TGGAAC|AGATC-5'
         I   G   F   V   G   V   V   V   Q   G   Q
``` restriction enzyme:

A/CTAGT
TGATC/A
SpeI

By cutting the incorporated oligonucleotide of the P1.7 epitope with SpeI followed by an insertion with the oligonucleotide of the P1.16 epitope (with SpeI sticky ends) the SpeI site disappears:

| left (SEQ ID NOS:21 and 22): | right (SEQ ID NOS:23 and 24): |
|---|---|
| 5'-ACTAGC\|TAT ACC-3'<br>3'-TGATCG\|ATA TGG-5' | 5'-ACC TTG\|TCTAGT-3'<br>3'-TGG AAC\|AGATCA-5' |

The used class 1 OMP gene in plasmid 2-2ΔSE contains a KpnI restriction-site in the part encoding loop 5. A P1.16 oligonucleotide has been placed therein. Through incorporation the KpnI restriction site disappeared. This construct is named pPH016.

TABLE C

| construct | in loop 6 | in loop 5 |
|---|---|---|
| pJB007 | P1.7 | |
| pJB016 | P1.16 | |
| pJB716 | P1.7.16 | |
| pPH016 | | P1.16 |

1.4.2.2 Transformation of constructs to *E. coli*

Subsequently transformation of the four constructs to *E. coli* K12 NN522 (see furtheron) was carried out. The transformants were grown under selective pressure of 100 μg/ml Ampicilline. Plasmid was isolated from the colonies formed (see furtheron) and checked for presence of the correct constructs. Construct PJB007 was checked for the disappeared KpnI and the formed SpeI site. The construct pBJ016 was checked for the disappeared KnpI and the formed SnaBI site and the construct pJB716 was checked for the disappeared SpeI site. With the aid of SDS-PAGE, Western blotting & immunoblotting (see furtheron) with the suitable monoclonals it was observed whether the insertions of the P1.7 and P1.16 epitope were successful therefore exhibiting expression and binding antibodies.

1.4.2.3 Transformation of constructs to meningococci

Subsequently the constructs (pJB007, pJB016, pJB716) were used to transform meningococcal strain A8-6' $B^-$ (P1.5,2), whereby recombination of the meningococcal chromosomal DNA and the construct occurred. With the aid of colony blotting and immunoblotting (see furtheron) $P1.7^+$ and the $P1.16^+$ colonies were isolated resulting in the desired strains after checking with SDS-PAGE, Western & Immunoblotting, see also Table C in results.

1.4.2.4 Checking of new strains with whole cell Elisa

The degree in which the incorporated epitopes were expressed in the strains J007, J016, J716, J072 and P016, was observed and this expression was compared to the expression of the parent strains.

1.4.3 Preparation & insertion of oligonucleotides

The complementary non phosphorylated oligonucleotides as indicated above, were synthesized on the Applied Biosystems 3814 DNA synthesizer. Hybridisation occured by adding the complementary oligonucleotides in equal concentrations, warming to 95° C. and subsequently cooling to room temperature. This led to oligo's with the correct sticky ends. The plasmid was digested with the correct enzyme, after which oligonucleotides were ligated with the aid of T4 ligates in the plasmid o/n at 15° C. (in the ratio 200 ng oligo/I μg plasmid). The ligation mixture was subsequently warmed to 80° C. and slowly cooled to room temperature to enable incorporation of oligonucleotide. Through incorporation of the oligo's in the plasmid the used restriction site disappeared. The ligation mixture was consequently cut with this enzyme, whereby linearizing the selfclosing products under the plasmids. Upon transformation to *E. coli* K12 NM522 (see furtheron) these linear pieces were degraded, so that all transformants must have an insertion. With the aid of SDS PAGE, Western blotting & immunoblotting (see furtheron) with monoclonals against the new epitopes the transformants were selected for the correct orientation of the incorporated oligonucleotide.

1.4.4 Transformation to *E. coli* K12 NM522

Transformation of plasmid DNA to *E. coli* was carried out according to [13]. For this an *E. coli* K12 NM522 was used which was grown in Luria Broth medium (Trypton 10 g/l; yeast extract 5 g/l; NaCl 10 g/l, pH 7.0) at 37° C. After transformation the *E. coli* was plated on a solid nutrition medium consisting of LB-medium with 1.5% (m/v) agar (Noble, Difco). For selection for ampicillin resistance 100 μg/ml ampicillin (Sigma) was added to the medium, after which growth occurred at 30° C. in order to prevent satellite formation.

1.4.5 Plasmid isolation

Plasmid isolation from *E. coli* was carried out according to the alkaline lysis method [13].

1.4.6 Agarose gel electrophoresis

Agarose gel electrophoresis was carried out according to [13]. For this 1% (m/v) (Sigma No A-9539) for a normal gel and a 1.2% (m/v) low melting agarose (Nusieve GTG, FMC Bioproducts) were applied for a preparative gel. TBE buffer (RIVM) 1× concentrated was applied as buffer for these gels: 0.089M Tris, 0.089M boric acid, 0.002M ETDA (pH 8.3). The molecular weight marker used here was the lambda HindIII digest (Boehringer Mannheim) with fragment sizes of 125, 564, 2027, 2322, 4361, 6557, 9416, 23130 bp. A 30% (m/v) sucrose solution with 0.25% (m/v) bromophenol blue served as loading buffer (5×). The electrophoresis was carried out at 10 V/cm. Afterwards these were coloured with 0.5 μg/ml ethidiumbromide and photographed.

1.4.7 Transformation to *Meningococci*

A plate with *Meningococci* was cultivated o/n with 5% $CO_2$ and damp tissue at 37° C. The cells of the fully cultivated plate were subsequently resuspended in 10 ml M üller Hinton medium (RIVM) with 10 mM $MgCl_2$ of 37° C. The bacterial suspension was subsequently diluted 1:5 in M üller Hinton medium, after which 1 μg/ml plasmid DNA was added. After incubation for 3 hours at 37° C., $10^4$ dilution in sterile PBS (with 0.01M phosphate, buffered physiological salt pH 7.2; RIVM) was carried out and plating on a gonococcal agar plate (* supplement 3) occurred. After overnight cultivation the correct transformants were selected with the aid of colony blotting. See furtheron, at colony blotting.

1.4.8 Colony blotting

The cells of a fully covered meningococcal plate were transferred to a 0.45 μm nitro cellulose membrane (Schleicher & Schuell). Subsequently the bacterial cells were put in PBS (phosphate buffered phys. saline, pH 7.2; RIVM) with 0.1% Tween 80 (Polyoxyethylene sorbitan monooleate, Merck) and inactivated for 1 hour at 56° C. Afterwards the excess cells were wiped off and the blot was treated as in immunoblotting (see furtheron).

1.4.9 SDS PAGE

SDS PAGE was carried out according to [8]. The gel consisted of a 5% (m/vol.) acrylamide stacking gel and an 11% (m/vol.) acrylamide resolving gel. The used reference proteins (RIVM) had the sizes 14, 20, 30, 43, 67 and 94 kD. All samples for the SDS PAGE consisted of complete cells.

For the *E. coli* cells these were cultivated o/n at 37° C. in LB-medium with 100 μg/ml ampicillin, with and without 1 mM IPTG (=isopropyl-B-D-thiogalactopyranoside, Sigma). Subsequently 1.5 ml of the suspension was centrifuged off. The pellet was suspended in 70 μl $H_2O$ to which 130 μl loading buffer (Tris/HCl 0.625M pH 6.8; 10% SDS; 50% glycerol; 0.01% bromophenol blue; B-mercapto-ethanol= 2.4:4:2:1) was added. The mixture was subsequently incubated for 10 min. at 95° C.

For the meningococcal cells from a fully cultivated plate (o/n, with 5% $CO_2$ and damp tissue at 37° C.) were dissolved in 10 ml PBS (with 0.01M phosphate, buffered physiological saline, pH 7.2; RIVM), inactivated for 30 min. at 56° C. and centrifuged off (10 min. at 4000 rpm). The pellet was suspended in 500 μl $H_2O$. 170 μl loading buffer and 0 to 35 μl $H_2O$ were added to 35 to 70 μl bacterial suspension, total volume of 200 μl. This mixture was warmed for 10 min. at 95° C. and put on gel.

The used electrophoresis buffer consisted of 50 mM Tris/HCl (pH 8.3); 380 mM glycine; 0.1% SDS. The electrophoresis was carried out at a constant current of 40 mA. After electrophoresis the gels were:

1. or coloured in 1 hour at 56° C. with Coomassie brilliant blue (0.1% (w/vol.) in 10% (vol./vol.) acetic acid and 30% (vol./vol.) methanol) and decoloured for at least 1 hour at 56° C. in a 10% (vol./vol.) acetic acid/5% (vol./vol.) methanol solution.
2. or blotted on a 0.2 μm nitro cellulose membrane (Schleicher & Schuell), see furtheron at Western blotting.

1.4.10 Western and immunoblotting

The proteins separated on SDS PAGE were transferred to a 0.2 μm nitrocellulose membrane (Schleicher & Schuell) with the aid of the Ancos Semi Dry Electroblotter A, for 1 hour at 0.8 mA/cm² gel, with 25 mM TRIS/HCl (pH 8.3); 192 mM glycerine; 20% methanol; 0.0375% SDS as blot buffer. Subsequently the blot was rinsed for a quarter of an hour in PBS (phosphate buffered physiological saline, pH 7.2) with 0.1% Tween 80 (Merck). Afterwards the blots were rinsed for half an hour in PBS 0.1% Tween and 0.3% caseine (hydrolysate, N-Z-AmineA, ICN Biochemicals). The blots were subsequently incubated for at least 1 hour in PBS/0.1% Tween/0.3% caseine with the monoclonal antibody against the epitope to be detected. After incubation it was rinsed 3×10 min. with PBS/0.1% Tween and subsequently incubated for half an hour with protein A peroxidase conjugate (diluted 1:10.000) [9]. After rinsing again for 3×10 min. with PBS/0.1% Tween and 1× with $H_2O$ the substrate/hydrogen peroxide mixture: 30 ml substrate A (substr. A: phosphate/citrate buffer, 0.02M $Na_2HPO_4$ and 0.01M citric acid 1:1, pH 5.0) with 10 ml substrate B (substr. B: 24 mg tetramethyl benzidine and 80 mg DONS (Dioctyl-sulfosuccinate) in 10 ml 96% ethanol) and 20 μl hydrogen peroxide 30% (Merck) were added. After a few minutes green/blue bands became visible on the blots where antibodies bind the proteins. Afterwards the blots were rinsed 3× with $H_2O$ and photographed.

1.4.11 Whole cell Elisa

A plate with *Meningococci* was grown o/n with 5% $CO_2$ and damp tissue at 37° C. The cells were subsequently resuspended in 5 ml PBS (phosphate buffered phys. saline, pH 7.2; RIVM) and inactivated for 30 min. at 56° C. Subsequently the suspension was diluted to an $OD_{620}$ of 0.1. Microtitre plates (Titertak PVC microassay plates U bottom) were filled with 100 μl suspension/well (coating). The suspension was dried o/n at 37° C. on for 2 days at room temperature. The plates were rinsed 3× with PBS with 0.1% Tween (Merck) shortly before use. 100 μl Solution with the monoclonal-antibody-dilution in PBS/0.1% Tween/0.5% Protifar (Nutricia) was added per well and incubated for 1 hour at 37° C. The plates were rinsed 3× with PBS/0.1% Tween. Subsequently the wells were filled with 100 μl protein A peroxidase conjugate (RIVM, 1:100000× dilution) or anti IgM* conjugate (RIVM, 1:2000× dilution in PBS/0.1% Tween/0.5% Protifar) suspension/well and incubated for 1 hour at 37° C. After rinsing 3× with PBS/0.1% Tween 100 μl substrate C (substr. C: 1 ml tetra methyl benzidine (6 mg/ml alcohol 96%) and 22 μl $H_2O_2$ 30% (Merck) in 60 ml 0.11M NaAc buffer) was added per well, after which incubation took place for 10 minutes. The reaction was stopped by blocking with 100 μl 2M $H_2SO_4$/well. The absorptions were read with an ELSIA reader (Biokinetics Reader EL312e of Bio-Tek Instruments) at 450 nm.

1.4.12 OMP isolation

A plate with *Meningococci* was grown o/n at 37° C. with 5% $CO_2$ and damp tissue. The cells were subsequently resuspended in 5 ml liquid meningococcal medium (RIVM) and divided over two flasks with 200 ml of meningococcal medium (RIVM). These flasks were shaken o/n at 37° C. The cells were inactivated 30 min at 56° C., after which they were centrifuged at 10,000 rpm for 10 min. (Beckman model J-21B, rotor JA-14). The top liquid was discarded and 10 ml 0.01M Tris/HCl pH 8.0 was added to every pellet. After resuspending the pellets the suspensions were joined in one 50 ml tube. The tube was placed in ice water and subsequently subjected to 15 min. ultrasonic vibration (Branson Sonifier 250, position 4, 50%). After which centrifugation was carried out for 30 min. at 4000 rpm (Heraeus Christ Minifuge GL with permanent rotor). The top liquid was centrifuged for 1 hour at 30,000 rpm and 10° C. (Sorvall ARC-1 ultracentrifuge Oil Turbine Drive (OTD)-65, rotor 70 $T_i$). Subsequently the pellet was resuspended in 4 ml 1% sarcosyl in Tris/HCl pH 8.0 and centrifuged for 15 min. at 5000 rpm (Heraeus minifuge). The top liquid was centrifuged for 1 hour at 30,000 rpm and 10° C. (Sorvall ultracentrifuge, rotor T865.1). After pouring of the top liquid the pellet was dissolved in 2 ml 0.01M Tris/HCl pH 8.0. Subsequently the yield was checked by determining the protein content (with the BCA* Protein Assay Reagent of Pierce, protocol according to the manufacturer). After which the OMP's were brought to a protein content of 1 mg/ml in Tris/buffer and filled out to 50 μl/tube. The purity is determined with the aid of an 11% SDS-PAA-gel and an ELISA.

1.5 Results

1.5.1 Control of pPH204 through transformation to Meningococci

In order to check whether the plasmid pPH204 remains intact, this plasmid was transformed to meningococcal strain H44/76 B⁻. Here the P1.2 epitope of plasmid pPH204 was exchanged with the P1.16 epitope of strain H44/76. Selection for the correct transformants took place by means of colony and immunoblotting, whereby P1.2⁺ colonies were isolated. The colonies provided the strain J072 after control with the aid of SDS-PAGE, Western immunoblotting. This strain has the P1.7 epitope in loop 1 and the P1.2 in loop 4.

1.5.2 Insertion of P1.7 oligonucleotide in the KpnI site of pPh204

The oligonucleotide for the P1.7 epitope was placed in the KpnI site of pPH204, after which the resulting construct pJB007 was transformed to E. coli K12 NM522. Plasmid was isolated from the resulting colonies. The isolated plasmid material was checked for disappearance of the KpnI restriction site and the presence of the new SpEI restriction site. In all checked transformants the KpnI restriction site had disappeared and the new SpeI restriction site was present. The transformants were place on SDS PAGE. After Western immunoblotting with monoclonal antibodies directed against the P1.7 epitope, 3 transformants comprising the oligonucleotide in the correct orientation were selected.

1.5.3 Insertion of P1.16 oligonucleotide in the KpnI site of pPH204

The oligonucleotide for the P1.16 epitope was placed in the KpnI site of pPH204 (construct pJB016) and subsequently transformed. Plasmids of transformants were checked for the disappearance of KpnI site and the new SnaBI site, see FIG. 10. Three transformants having the P1.16 epitope in the correct orientation were selected with Western immunoblotting, see FIGS. 11 and 12, 13, 14, and 15.

1.5.4 Isolation of P1.16 oligonucleotide in the SpeI site of pJB007

The oligonucleotide for the P1.16 epitope was placed in the SpeI site of PJB007 (construct pJB716) and transformed. Plasmids of transformants were checked for the disappearance of SpeI site. 1 Transformant having the oligonucleotide in the correct orientation was selected with Western immunoblotting.

1.5.5 Insertion of P1.16 oligonucleotide in the KpnI site of 2-2ΔSE

The oligonucleotide for the P1.16 epitope was placed in the KpnI site of plasmid 2-2ΔSE (construct pPH016) and transformed. Plasmids of transformants were checked for the correct incorporation of the oligonucleotide (data not included) [17].

1.5.6 Transformation of the constructs to Meningococci

Subsequently the four constructs pJB007, pJB016, pJB716 and pPH016 were transformed to meningococcal strain A806ʳ B⁻ (P1.5.2). Selection for the correct transformants occurred by means of colony and immunoblotting, whereby P1.7⁺ and P1.16⁺ colonies were isolated. This resulted after checking the strains according to Table D.

TABLE D

| constructed meningococcal strains | | | | |
|---|---|---|---|---|
| meningococcal strain | in loop 1 | in loop 4 | in loop 5 | in loop 6 |
| J007 | P1.5 | P1.2 | | P1.7 |
| J016 | P1.5 | P1.2 | | P1.16 |
| J716 | P1.5 | P1.2 | | P1.7.16 |
| J072 | P1.7 | P1.2 | | |
| P016 | P1.5 | P1.2 | P1.16 | |

1.5.7 Whole cell ELISA

The expression of the incorporated epitopes in the new strains was observed and compared with the parent strains A8-6ʳ (P1.5.2) and H44/76 (P1.7.16) Table D.

1.6 Conclusion & discussion

In this series of tests four new meningococcal strains were made with extra epitopes in loops 5 and 6. Strains J007 and J016 respectively contain the 1.7 and the P1.16 epitope in loop 6, whereas J716 carries both the P1.7 and P1.16 epitopes. Strain P016 contains the P1.16 epitope exclusively in loop 5. The whole cell ELISA carried out shows that the monoclonal antibodies directed against the incorporated epitopes bind well to reasonably well to the whole cells in comparison to the parent strains H44/76 and A8-6ʳ. The ELISA shows that the new class 1 OMP's can be transported completely antibodies would occur. When strain H44/76 is compared to the four strains with extra epitopes in loops 5 and 6, the P1.7 epitope appears to bind equally well in all cases. It does not matter whether the P1.7 epitope is located in loops 1, 5 or 6.

1.7 Literature for Example I

[1] Barlow A. K., Heckels J. E. and Clarke I. N., The class 1 outer membrane protein of Neisseria meningitidis: gene sequence and structural immunological similarities to gonococcal porins, Molecular Biology 1989, 3(2), p. 131–139.

[2] Frasch E. F., Zollinger W. D. and Poolman J. T., Serotyping antigens of Neisseria meningitidis and a proposed scheme for designation of serotypes, Reviews of infectious diseases, vol. 7, no. 4, July-August 1985, p. 504–510.

[3] Gotschlich E. C., Meningococcal meningitis, In: Bacterial Vaccins (Ed. Germanier, R.), Acedemice Press; Inc, 1984, ch.8, p. 237–255

[4] Maiden M. C. J., Suker J., McKenna A. J., Bygraves J. A. and Feavers I. M., Comparison of the class 1 outer membrane proteins of eight serological reference strains of Neisseria meningitis, Molecular Microbiology(1991), 5(3), p. 727–736

[5] Klugman K. P., Gotschlich E. C. and Blake M. S., Sequence of the structural gene (rpmM) for the class 4 outer membrane protein of Neisseria menigitidis, homology of the protein to gonococcal protein III and Escherichia coli Omp A and construction of meningococcal strains that lack class 4 protein, Infection and Immunity, July 1989, p. 2066–2071.

[6] Ley P. van der, Heckels J. E., Virji M., Hoogerhout P. and Poolman J. T., Topology of outer membrane porins in pathogenic Neisseria, in press.

[7] Lifely M. R., Moreno C. and Lindon J. C., An intergrated molecular and immunological approach toward a meningococcal group B vaccine. Vaccine, vol. 5, March 1987, p. 11–26

[8] Lugtenberg B., Meijers J., Peters R., Hoek P. van de, Alphen L. van, Electrophoretic resolution of the major outer membrane protein of Escherichia coli K12 into four bands, FEBS letters, 1975, vol. 58, no.1, p.254–258.

[9] Nakane P. K., Kawaoi A., Perosidase-labeled antibody. A new method of conjugation, J. Histochem. and Cytochem.,1974, no. 22, p. 1084–1091.

[10] Nester E. W. Evans Roberts C., Pearsall N. N. and McCarthy B. J., Microbiology 2nd edition, Eastbourne, Sussex, Holt Rinehart and Winston, 1978, p. 433, 443, 474, 540–543, 591.

[11] Peltola H., Safary A., Käythy H., Karanko V. and André F. E., Evaluation of two tetravalent (ACYW-135) meningococcal vaccines in infants and small children: a clinical study comparing immunogenity of O-acetyl-negative and O- acetyl-positive grou C polysaccharides.

[12] Poolman J. T., Marie S. and Zanen H. C., Variability of low molecular weight, heat modifiable outer membrane proteins of *Neisseria Meningitidis*, Infection and Immunity, December 1980, p. 642–648

[13] Sambrook J., Fritsch E. F. and Maniatis T., Molecular cloning: a laboratory manual, 2nd edition, 1989, Cold Spring Harbour Laboratory, Cold Spring Harbour, N.Y. p.1.25–1.28, 1.82–1.84, 6.3–6.16, 6.18–6.19.

[14] Saukonen K., Leinonen M., Abdillahi H. and Poolman J. T., Comparative evaluation of potentional components for group B meningococcal vaccine by passive protection in the infant rat and in vitro bacterial assay, Vaccin. vol. 7, August 1989, p. 325–328.

[15] Tomassen J., Vermeij P., Struyvé M., Benz R. and Poolman J. T., Isolation of *Neisseria meningitidis* mutants deficient in class 1 (PorA) and class 3 (PorB) outer membrane proteins, Infection and Immunity, May 1990, p. 1355–1359.

[16] Tsai C. M., Frasch C. E. and Mocca L. F., Five structural classes of major outer membrane proteins in *Neisseria meningitidis*, J. Bacteriol., 1981, no. 146, p.46–78.

[17] P. van der Ley personal information.

EXAMPLE II

Summary

In this example the creation of a mutated outer membrane protein is described, which OMP offers a coupling possibility for coupling the class 1 OMP to the oligosaccharide part of the lipopolysaccharide. For this reason an oligonucleotide encoding a cysteine is incorporated in an existing restriction site of the class 1 protein gene, said oligo is subsequently transformed to a capsule deficient mutant of meningococcal strain H44/76, H44/76-B$^-$. After transformation cysteine incorporation did not appear to have any influence on epitope expression or an production of the class 1 OMP.

The selection of loops 5 and 6 was determined by the fact that they contain no important class 1 epitopes and by the maintenance of immuno activity illustrated in Example I after providing mutations in these loops. Checking the result of incorporation took place on the basis of epitope expression of the resulting transformants.

2.1 Material

The used plasmid:

The used plasmid, pPH204, is derived from the pTZ19R plasmid of Pharmacia.

OVERVIEW OF THE CREATION OF THE USED PLASMIDS

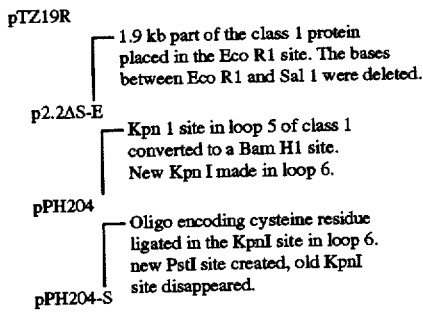

Used enzyms:

KpnI (vol. act.: 10 U/µl); with incubation-buffer L.

PstI (vol. act.: 10 U/µl); with incubation-buffer H.

T4 DNA Ligase (vol.act.: 1 U/µl); with T4 DNA LIGASE buffer.

The composition of the corresponding incubation buffer, see Table E.

TABLE E

| Composition of used buffers | | | |
|---|---|---|---|
| Buffer components in mmol/l | H | L | T4 DNA Ligase |
| Tris-HCl | 50 | 10 | 66 |
| MgCl$_2$ | 10 | 10 | 5 |
| NaCl | 100 | | |
| Dithioerytheritol | 1 | 1 | 5 |
| ATP | | | 1 |
| pH at 37° C. | 7.5 | 7.5 | 7.5 |

Both the enzymes and buffers are derived from BOEHRINGER MANNHEIM.

Used bacteria:

*Escherichia coli* K12 NM522: this strain does not comprise a restriction modification system.

Meningococcal strain: H44/76-B$^-$. This is the mutation of H44/76 lacking a capsule.

Used monoclonals: see Table F.

TABLE F

| Used monoclonals | |
|---|---|
| monoclonal | directed against |
| MN16C13F4 | P1.2 |
| MN14C11.6 | P1.7 |
| MN5C11G | P1.16 |

All used monoclonals are derived from the RIVM.

Used membrane:

For Western Blot

BIO RAD Trans Blot Transfer medium pure Nitro cellulose membrane

Blotting Filter Paper, 0.45 micron.

Lot.No.: 4072/87020

Cat.No.: 162-0113

For Colony Blot

SCHLEICHER & SCHUELL BA 85/22, 0.45 micron.

diameter: 82 mm

Ref.No.: 406 216

2.2 Methods

2.2.1 Hybridisation of Oligonucleotides

The complementary nonphosphorylated oligonucleotides (OLIGO'S) (see below) were added in a concentration of 1 µg/100 µl each, and warmed to 95° C. After warming the mixture was able to slowly cool down to room temperature. Beacause the cooling down occurs slowly hybridisation of the complementary oligonucleotides can occur [5]. In this manner oligo's with the correct sticky ends are created, i.e. KpnI sticky ends.

Information C1–C2 Oligonucleotide

Oligonucleotide encoding cysteine with KnpI sticky ends (SEQ ID NOS:25–28)

```
        Gly   Cys   Ser   Leu   Ser
5'-   G GGC   TGC   AGC   CTA   AGT    AC-3'
3'-CATG C CCG   ACG   TCG   GAT   T      -5'
        Ala   Ala   Ala   End
Restriction site for KpnI:     5'-GGTACC-3'
                               3'-CCATGG-5'
Restriction site for PstI:     5'-CTGCAG-3'
                               3'-GACGTC-5'
```

The oligonucleotides is composed of two single-stranded oligonucleotides:

Oligo C1 (SEQ ID NO:29) 5'-GGG CTG CAG CCT AAG TAC-3'

Oligo C2 (SEQ ID NO:30) 5'-TTA GGC TGC AGC CCG TAC-3'

2.2.2 Ligation of Hybridised Oligonucleotides in Plasmids

The plasmids were subjected to digestion with the correct enzyme and subsequently separated on a 1.2% low melting gel from the plasmids that were not cut. Afterwards the gel was coloured with ethidium bromide and the cut plasmids were cut out of the gel. After which the cut plasmid DNA was isolated from the agarose gel again through phenol extraction and ethanol precipitation [8].

Half of the isolated plasmids were taken for ligation of the oligo's. The ligation mixture was composed as follows: 50 µl, cut plasmid DNA, 20 µl hybridised oligo mixture, 10 µl ligation buffer, 4 µl $T_4$ ligase, 16 µl $dH_2O$. After incubation of the ligation mixture overnight (o/n) at 16° C. the mixture was concentrated by ethanol precipitation. Subsequently the ligation products were separated on a 1.2% low melting gel and the ligation products were cut out after which they were isolated from the gel by phenol extraction and ethanol precipitation.

2.2.3 Melting Excess Oligo

After isolation of the ligation products from the gel these were warmed to 65° C. so the excess oligo was melted. By slowly cooling the mixture down again hybridisation could occur between the complementary parts of the oligo ligated to the plasmid.

2.2.4 Removal of Selfclosing Plasmids

The solutions were subsequently postcut with the original restriction enzyme in order for the selfclosing plasmids to be reopened. This postcutting could take place as the incorporation of the oligo had changed the original restriction site to a different restriction site. After cutting linear plasmids without oligo and circular plasmids with an incorporated oligonucleotide were created. As only circular plasmid DNA can be taken in by E. coli, in principle only transformants containing the oligo can arise.

2.2.5 Transformation to E. coli

Transformation procedure see: [8].

After transformation the transformants were plated on Luria Broth (L.B.) medium nutrition media to which 100 µg/ml ampicillin was added. The plates were incubated o/n at 37° C., after which the transformants were plated from single colonies on L.B. nutrition media with ampicillin and incubated again o/n after which single colonies were transferred to liquid L.B. medium with ampicillin, which mixture was incubated o/n at 37° C. whilst being shaken and was used for plasmid isolation (see furtheron).

2.2.6 Plasmid Isolation

Plasmid isolation from the transformants was carried out according to the alkaline lysis method [8].

2.2.7 Digestion of the Recombinant-Plasmids

In order to check whether the oligonucleotide was present in the plasmids, a digestion was carried out with the restriction enzyme encoding the new restriction site. A digestion was also carried out with the restriction enzyme encoding the restriction site which should have disappeared, so that it could be determined on the basis of the restriction pattern on an agarose gel whether the old restriction site had disappeared and the new site was really present. The protein composition of the positive transformants was checked with sodium dodecyl sulphate polyacrylamide gel electrophoresis (SDS, PAGE).

2.2.8 SDS PAAGE

The SDS PAAGE was carried out according to protocol [8]. An 11% acrylamide gel was used as separation gel, a 5% acrylamide gel was used as concentration gel.

Procedure with E. coli

The positive transformants were grown for electrophoresis o/n in liquid LB medium with (100 µg/ml) ampicillin both with and without (1 mM) IPTG {=isopropyl-8-D-thiogalactopyranoside (Sigma)}. 1.5 ml of the o/n culture was centrifuged off, after which the pellet was resuspended in 40 µl $dH_2O$, to which 10 µl loading buffer {250 mM Tris-HCl pH 6.8, 10% SDS, 10% dithiotreitol, 50% glycerol, 0.05% bromophenol blue} were added, after which the suspension was warmed for 10 minutes at 95° C. and put on gel.

Procedure with Meningococci

For the Meningococci the grown o/n in a damp atmosphere with 5% $CO_2$ on a meningococcal plate enriched with isovitalex were suspended in 10 ml PBS (0.01M phosphate buffered physiological saline, pH 7.2: RIVM). The obtained suspension was subsequently warmed for 30 min. at 56° C., in order for the Meningococci to be inactivated after which the suspension was centrifuged off (10 minutes at 4000 rpm). The pellet was suspended in 40 µl $dH_2O$ and to which 10 µl loading buffer was again added after which the suspension was warmed for 10 min. at 95° C. and put on gel.

The applied electrophoresis buffer had the following composition: 50 mM Tris/HCl (pH 8.3), 380 mM glycine, 0.1% SDS. The electrophoresis was carried out with 20 mA per gel.

After the electrophoresis the gel was:

1) coloured with Coomassie brilliant blue (1 hour at 56° C.), and afterwards coloured with 10% HAc/5 (vol./vol.)% methanol (3 times 30 min. at 56° C.).
2) blotted on a 0.45 micron nitrocellulose membrane (Biorad).

2.2.9 Western or Immunoblotting

With the aid of an Ancos Semi Dry Electroblotter A the proteins of the SDS PAAgel were blotted over on to a 0.45 micron nitrocellulose membrane (Biorad). The protein transport from the gel to the membrane occurred by blotting for 1 hour at 0.8 mA/cm$^2$ gel whereby 25 mM Tris-HCl (pH 8.3), 192 mM glycine, 20% methanol, 0.0375% SDS was used as blot buffer.

After blotting the blot was rinsed for a quarter of an hour in PBS with 0.1% Tween 80 (polyoxyethylene sorbitan monooleate, Merck). Subsequently the blot was rinsed for half an hour with PBS to which 0.1% Tween 80 and 0.3% caseine hydrolysate (N-Z Amine A, ICN Biochemicals) was added, after which incubation occurred for an hour with monoclonals dissolved in PBS/0.1% Tween 80/0.3% caseine, against the epitope to be detected. After which the blot was rinsed 3 times for 10 min. with PBS/0.1% Tween 80 after which it was incubated for half an hour with protein A peroxidase conjugate, diluted 1:10.000 with PBS/0.1% Tween 80/0.3% caseine. Subsequently rinsing again took place 3 times 10 min. with PBS/0.1% Tween 80 and once with $d^{H2}O$ after which the hydrogen peroxide substrate mix (20 µl 30% hydrogen peroxide, Merck; 30 ml substrate A:phosphate/citrate, 0.02M $Na_2HPO_4$ and 0.01M citric acid (1:1) pH=5.0; 10 ml substrate B:80 mg Dioctyl-sulphosuccinate (DONS), 24 mg tetra methyl benzidine (TMB) in 10 ml 96% ethanol) were added.

After several minutes blue bands became visible at the position where the monoclonal antibodies had bound to the corresponding proteins. Afterwards the blots were rinsed another 3 times with water after which they were photographed or were kept in the dark until they were photographed.

2.2.10 Transformation to Meningococci

Meningococci were grown o/n on GC agar (Difco), enriched with isovitalex at 37° C. in a damp atmosphere with 5% CO$_2$ (3). the cells of the completely covered plate were resuspended in 10 ml Müller Hinton medium (RIVM), with 10 mM MgCl$_2$ of 37° C. Subsequently the suspension was diluted 1:5 in Müller Hinton medium with 10 mM MgCl$_2$ and 1 µg/ml plasmid DNA was added. Subsequently incubation for 3 hours at 37° C. took place after which the bacterial suspension was diluted 10$^4$ times with sterile PBS and plated on a GC plate. After cultivation o/n the correct transformants were selected by means of a colony blot.

2.2.11 Colony Blot

The colonies of a plate covered o/n at 37° C. in a damp atmosphere with 5% CO$_2$ were blotted over on to a 0.45 micron nitrocellulose membrane (Schleicher & Schuell). Subsequently the blot was warmed for 30 min. in PBS/0.1% Tween 80 at 56° C. in order for the Meningococci to be inactivated. After warming the excess bacteria were wiped off. For the further procedure see the Western or immunoblot technique.

2.2.12 OMP Isolation

A plate with Meningococci was grown o/n at 37° C. in a damp atmosphere with 5% CO$_2$ after which the cells were resuspended in 5 ml meningococcal medium. 200 ml Meningococcal medium was seeded with 2.5 ml of the mixture. These 200 ml were activated o/n at 37° C., after which the Meningococci were inactivated by incubation during half an hour at 56° C. Subsequently the Meningococci were pelleted by centrifuging the medium for 10 min. at 10.000 rpm (centrifuge: centrikon T-324, rotor A6.9). The supernatant was poured off and the pellet was resuspended in 10 ml 0.01M Tris/Hcl pH 8.0. Subsequently this solution was ultrasonically vibrated for 15 min. (Branson Sonifier 250, position 4, 50%) whereby the solution was placed in an icebath. Subsequently the sonified solution was centrifuged at 10 min. at 5000 rpm (centrifuge: centrikon T-324, rotor A8.20). The supernatant was subsequently centrifuged for one hour at 20.000 rpm. and 10° C. (centrifuge: centrikon T-324, rotor A8.20). The pellet thus formed was resuspended in 4 ml 1% sarcosyl in 0.01M Tris/HCl pH 8.0, after which centrifugation took place for 5 min. at 5000 rpm. The supernatant was subsequently centrifuged for one hour at 20.000 rpm. and 10° C. (centrikon T-324 centrifuge, rotor A8,20). The thus formed pellet was resuspended in 1 ml 0.01M Tris/HCl pH 8.0. The yield was determined with the Microassay Procedure (BIORAD). The purity of the OMP's was checked with SDS PAAGE.

2.2.13 Transformant Check with the Aid of Polymerase Chain Reaction

Day 1

The Meningococci for undergoing PCR were seeded from a GC plate, enriched with isovitalex, and cultivated o/n in a damp atmosphere with 5% CO$_2$ at 37° C.

Day 2

A cell suspension was made of each of the strains to be subjected to PCR by resuspending a small flock of bacteria in 1 ml sterile distilled water and subsequently warming this suspension for 10 min. at 95° C. The resulting solution was subsequently shortly centrifuged and kept on ice. The reaction mixture was composed as follows:

10 µl buffer (500 mM KCl, 100 mM Tris/HCl pH 8.3, 15 mM MgCl$_2$, 0.1% {w/vol.} gelatine)
200 µM of each of the dNTP's
100 mg of each of the primers
25 µl cell suspension
filled to 100 µl with sterile distilled water.

100 µl mineral oil.
The PCR conditions were as follows: see Table G

TABLE G

| | PCR conditions | | |
|---|---|---|---|
| Cycle number | min. 95° C. | min. 55° C. | min. 72° C. |
| 1 | 5 | 1 | 2 |
| 2–30 incl. | 1 | 1 | 2 |

After the 30th cycle the samples were held for a further 8 minutes at 72° C. in order to make all the DNA present in the samples double-stranded.

After PCR the samples were subjected to a phenol extraction and an ethanol precipitation in order to obtain the produced DNA in pure form.

Day 3

10% of the purified DNA was electrophorated on a 0.1% agarose gel in order to observe the result. From this it should be apparent whether the incorporated nucleotide was present in the DNA.

2.2. Result 2.2.1 Transformation of the Recombinant Plasmids to E.coli

The hybridised oligonucleotide was ligated in pPH204 cut with KpnI after which the whole was transformed to E. coli K12 NM522. The plasmids were isolated from the resulting transformants. The isolated plasmids were cut with KpnI and PstI and subsequently electrophorated on a 0.8% agarose gel.

TABLE H

| Further illustration of FIG. 16 | | |
|---|---|---|
| lane number | sample description | remark |
| 1,6,11,21,26 | recombinant plasmid DNA | uncut |
| 2,4,7,9,12,14, 17,19,22,24,27 3,5,8,10,13,15, 18,20,23,25,28 | recombinant plasmid DNA KpnI digest recombinant plasmid DNA PstI digest | KpnI site should have disappeared through incorporation of the oligo a second PstI site has resulted, now a fragment is cut out of the plasmid |
| 16 | Lambda marker | HindIII digest |

From the formation of a fragment of approx. 600 base pairs from the PstI digest and the disappearance of the KpnI site it is apparent that the oligo has been incorporated in pPH204.

The transformants were subsequently cultivated o/n at 37° C. in liquid L.B. medium with 1 mM IPTG and 100 µg/ml ampicillin. The bacterial proteins were subsequently separated with the aid of SDS PAGE after which immunoblotting was used to see whether the oligo had been incorporated in the correct orientation. Using the blotting the size of the class 1 protein was observed by demonstrating the P1.2 epitope with the monoclonal MN16C13F4.

The transformants in the lanes No. 1, 3, 5, 7, 9, 11 show a protein band which has travelled less far than those of the transformants in the remaining lanes. This indicates that the produced protein is larger than in transformants in the lanes No. 2, 4, 6, 8, 10. The transformants in the odd lanes comprise the oligonucleotide in the correct orientation and those of the even lanes in the incorrect orientation, thereby creating a stop codon resulting in a smaller protein.

2.3. Transformation to H44/76 B⁻

The plasmids of the positive transformants were subsequently transformed to H44/76 B⁻, a capsule deficient mutant of H44/76. The transformants were selected by colony blotting for the P1.2 epitope with the monoclonal MN16C13F4. The outer membrane proteins of the pure transformants were isolated. The purity was checked by means of SDS PAAGE and immunoblotting. It was also checked whether the ratio between the class 1 protein and the other proteins had changed with the transformants. This appeared not to be the case (results not included).

Subsequently it was checked whether the P1.16 epitope had disappeared from the transformants, as a test the monoclonals against the P1.2 and the P1.7 epitopes were included as well as strain H44/76 B⁻ as test strain.

The monoclonal MN5C11G directed against the P1.16 epitope, only reacts with the parent strain. The monoclonal MN14C11.6 directed against the P1.7 epitope reacts with both the parent strain and the transformants. MN16C13F4 directed against the P1.2 epitope only reacts with the transformants.

2.4 Conclusion

The successful introduction of a cysteine residue in the class 1 protein of H44/76-B⁻ is apparent from the following results:

1) upon incorporation of the oligonucleotide the KpnI site has disappeared and a new PstI site has been formed.
2) after transformation to H44/76-B⁻ this has changed from P1.7.16 to P1.7,2 which is indicative of the fact that the gene encoding class 1 protein present in plasmid pPH204 in which gene the oligo was incorporated has been introduced into the Meningococcus. Cysteine incorporation does not appear to have an influence on the production of the class 1 protein considering the amount produced by the Meningococcus. The epitope expression by the bacteria also appears to remain normal.

2.5 Literature List for Example 2

1 FRASCH, C. E. 1977. Role of protein serotype antigens in protection against disease due to *Neisseria meningitidis*. J.Infect.Dis. 136 (suppl) S84–S90.

2 FRASCH, C. E., W. D. ZOLLINGER and J. T. POOLMAN. 1985. Serotype antigens of *Neisseria meningitidis* and a proposed scheme for designation of serotypes. Rev.Infect.Dis.7:504–510

3 GRIFFISS, J. M., B. L. BRANDT, D. D. BROUD, D. K. GOROFF AND C. J. BAKER. 1984. Immune response in infant children to disseminated infections with *Neisseria meningitidis*. J. Infect. Dis. 150:71–79.

4 KIM. J. J., R. E. MANDRELL, H. ZHEN, M. A. J. WESTERINK, J. T. POOLMAN and J. M. GRIFFISS. 1988, Electromorphic characterization and description of conserved epitopes of the lipooligosaccharides of group A *Neisseria meningitidis*. Infect.Immun. 56:2631–2638.

4A KLUGMAN, K. P., GOTSCHLICH, E. C. and BLAKE, M. S. 1989. Sequence of the structural Gene (rmpM) for the class 4 outer Membrane Protein of *Neisseria meningitidis*, Homology of the protein to Gonococcal Protein III and *Esscherichia coli* OmpA and Construction of meningococcal strains that lack Class 4 protein. Infect. and Immun., July 1989, P2066–2071.

5 LEY, P. van der, personal information.

5A MAIDEN, M. C. J., J. SUKER, A. J. McKENNA, J. A. BYGRAVES and I. M. FEAVERS. 1991. Comparison of the Class I outer membrane proteins of eight serological reference strains of *Neisseria meningitidis*. Molec. Microbiol. 1991. 5:3:P727–736.

6 POOLMAN, J. T. 1990. Polysaccharides and Membrane vaccines, Bacterial Vaccines, P57–86 (70).

7 POOLMAN, J. T., C. T. P. HOPMAN, and H. C. ZANEN, 1982. Problems in the defenition of meningococcal serotypes. FEMs Microbiol. Lett. 13:339–348.

8 SAMBROOK, FRITSCH, MANIATIS. Molecular Cloning, a laboratorium manual, second edition, Cold Spring Harbour Laboratory, N.Y. P1.25–1.28, P1.82–1.85, P6.3–6.16, P6.18–6.19, P18.47–18.55.

9 SAUKONEN, K., M. LEINONEN, H. ABDILLAHI and J. T. POOLMAN, 1989. Comparative evaluation of components for group B meningococcal vaccine bij passive protection in the infant rat and in vitro bactericidal assay. Vaccine 7:325–328.

10 TSAI, C. M., C. E. FRASCH AND L. F. MOCCA. 1981. Five structural classes of major outer membrane proteins in *Neisseria meningitidis*. J.Bacteriol. 146:89–78.

11 VEDROS, N. A. 1987. Development of meningococcal serogroeps. p.33–38 N. A. Vedros (ed.). Evolution of meningococcal disease, vol.2. CrC Press Inc., Boca Raton, Fla.

12 ZOLLINGER, W. D., and R. E. MANDRELL. 1977. Outer membrane protein and lipopolysaccharide serotyping of *Neisseria meningitidis* by inhibition of a solid phase radio-immunoassay. Infect.Immun.18:424–433.

We claim:

1. A B cell activating molecule capable of providing immunity against meningococcal disease, said molecule being derived from a meningococcal, lipopolysaccharide (LPS) with at least one B cell activating epitope, said molecule comprising the lipid A part of the LPS and at least one communal part of the oligosaccharide part (core region) of lipopolysaccharides specific for at least two meningococcal immunotypes, wherein at least the terminal galactose residue of the lacto-N-neotetraose unit of the LPS is absent in the molecule.

2. Molecule according to claim 1, said molecule being derived from the L3 core and having the following structure:

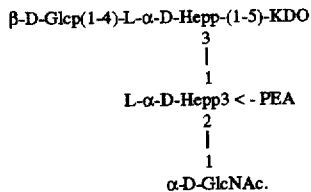

3. Molecule according to claim 1, said molecule being derived from the L2 core and having the following structure:

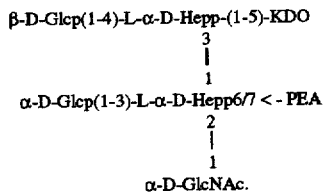

4. A molecule according to claim 1, said molecule being derived from the L3 core and having the following structure

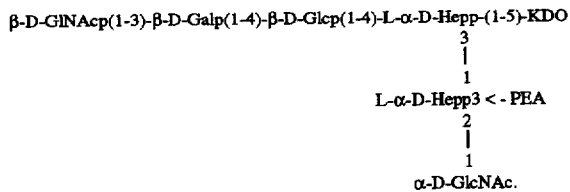

5. A molecule according to claim 1, said molecule being derived from the L2 core and having the following structure

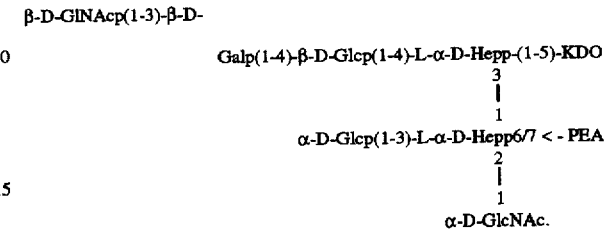

6. A molecule according to claim 1, wherein the meningococcal immunotypes are L2 and L3.

7. A B cell activating molecule capable of providing immunity against meningococcal disease, said molecule being derived from a meningococcal, lipopolysaccharide (LPS) with at least one B cell activating epitope, said molecule comprising the lipid A part of the LPS and at least one communal part of the oligosaccharide part (core region) of lipopolysaccharides specific for at least two meningococcal immunotypes, wherein at least one galactose residue of the lacto-N-neotetraose unit of the LPS is absent in the molecule, and wherein at least one glucose residue of said lacto-N-neotetraose unit of the LPS is retained in the molecule.

8. A method for preparing a molecule according to claim 1, wherein recombinant DNA techniques are used.

9. A method according to claim 8, wherein the molecule is obtained from a mutagenised production strain producing at least LPS without terminal galactose.

10. A method according to claim 8, wherein the molecule is obtained from a mutagenised production strain producing at least LPS without galactose.

11. A method according to claim 8, wherein the molecule is obtained from a mutagenised meningococcal production strain without galactose.

12. A method according to claim 8, wherein the molecule is obtained from a mutagenised production strain without galE.

13. A method according to claim 8, wherein the molecule is obtained from a mutagenised production strain without functional galE.

* * * * *